(12) United States Patent
Iwase et al.

(10) Patent No.: US 12,383,135 B2
(45) Date of Patent: Aug. 12, 2025

(54) IMAGE PROCESSING APPARATUS, IMAGE PROCESSING METHOD, AND STORAGE MEDIUM

(71) Applicant: CANON KABUSHIKI KAISHA, Tokyo (JP)

(72) Inventors: Yoshihiko Iwase, Kanagawa (JP); Osamu Sagano, Tokyo (JP); Hiroki Uchida, Tokyo (JP); Juun Horie, Tokyo (JP); Riuma Takahashi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 799 days.

(21) Appl. No.: 17/491,274

(22) Filed: Sep. 30, 2021

(65) Prior Publication Data

US 2022/0110521 A1 Apr. 14, 2022

(30) Foreign Application Priority Data

Oct. 8, 2020 (JP) .................................. 2020-170761
Oct. 8, 2020 (JP) .................................. 2020-170762

(51) Int. Cl.
*A61B 3/12* (2006.01)
*A61B 3/00* (2006.01)
*A61B 3/10* (2006.01)

(52) U.S. Cl.
CPC .......... *A61B 3/1233* (2013.01); *A61B 3/0058* (2013.01); *A61B 3/102* (2013.01)

(58) Field of Classification Search
CPC ...... A61B 3/0058; A61B 3/102; A61B 3/1233
See application file for complete search history.

(56) References Cited

FOREIGN PATENT DOCUMENTS

| JP | 2013153881 A | 8/2013 |
|----|--------------|--------|
| JP | 2017074325 A | 4/2017 |
| JP | 2018171141 A | 11/2018 |
| JP | 2019180692 A | 10/2019 |

*Primary Examiner* — Jack Dinh
(74) *Attorney, Agent, or Firm* — Canon U.S.A., Inc. IP Division

(57) ABSTRACT

An apparatus includes an obtaining unit configured to obtain, using an optical coherence tomography, an analysis map for a disk and an analysis map for a macular area, which are analysis results of three-dimensional data obtained by capturing an image of a region of a fundus of a subject's eye that includes the disk and the macular area, and a control unit configured to cause a display unit to display side by side a two-dimensional image of the region including the disk and the macular area, the analysis map for the optic disk, and the analysis map for the macular area.

11 Claims, 18 Drawing Sheets

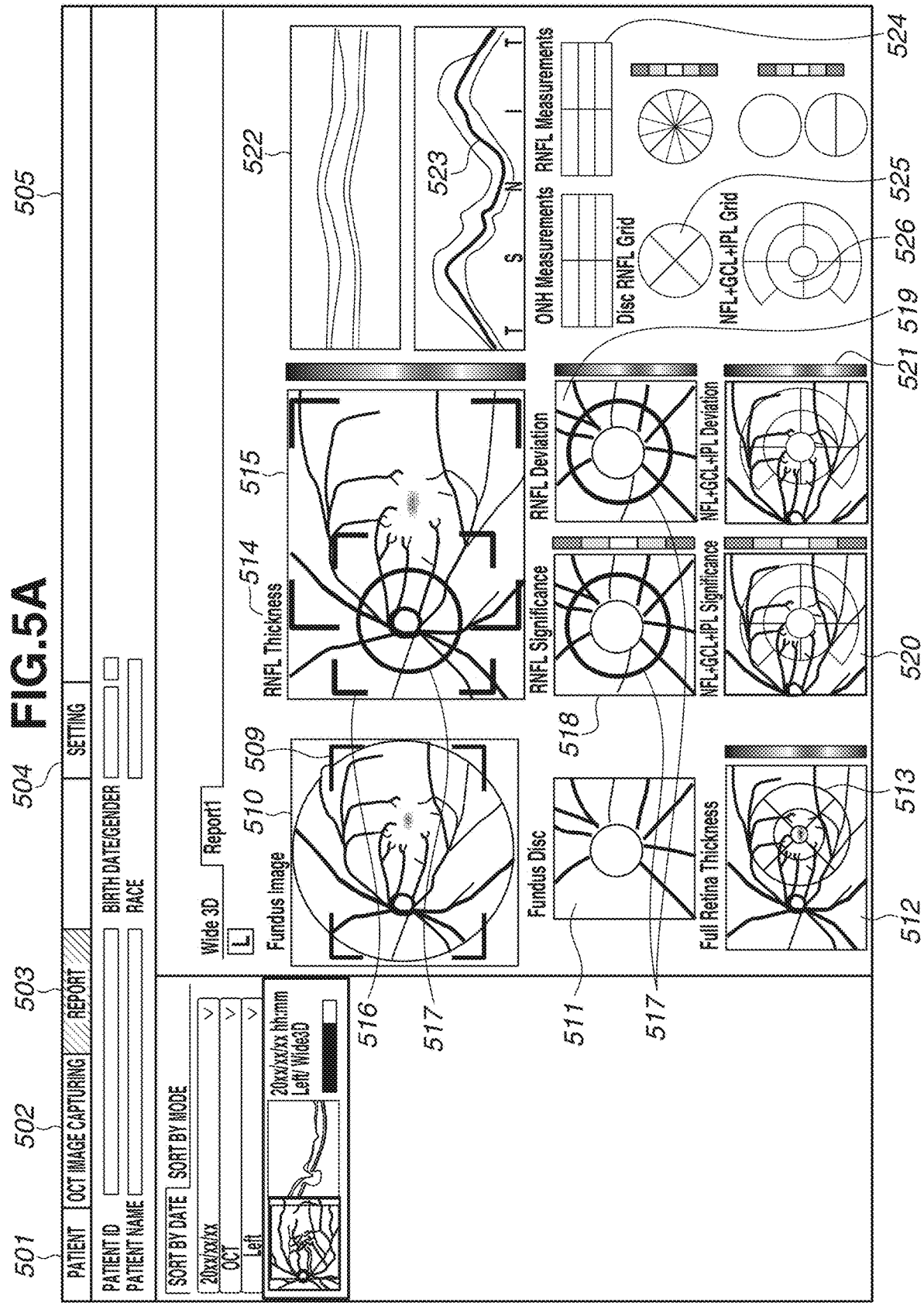

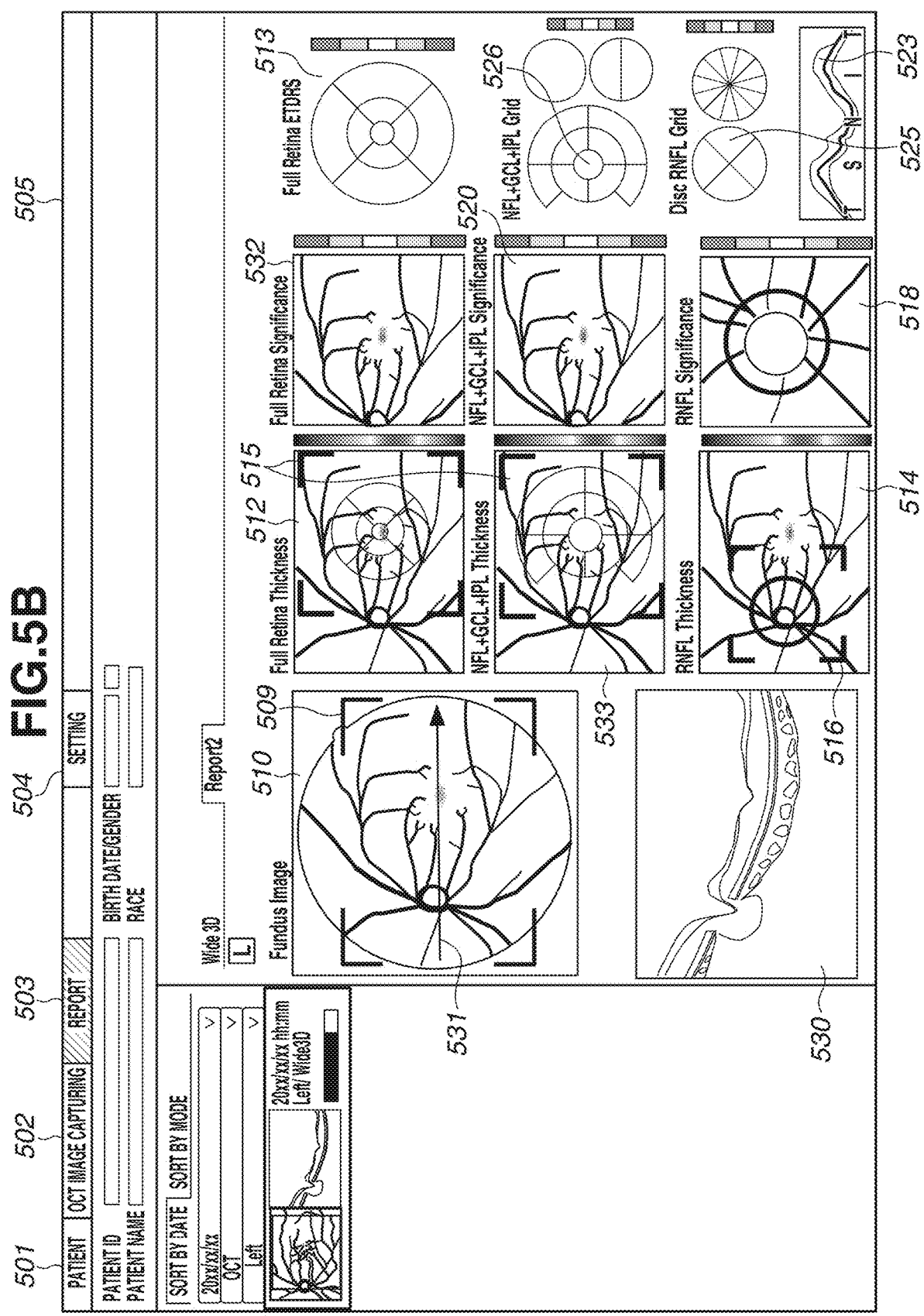

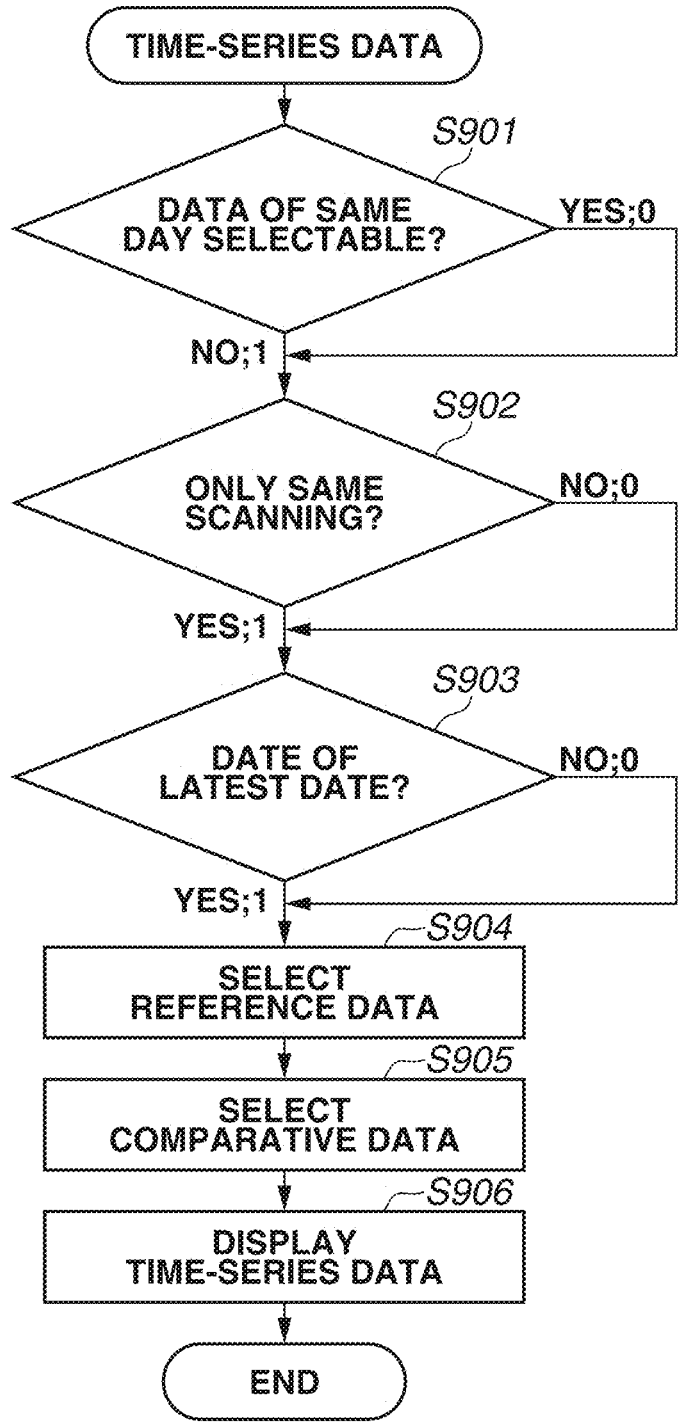

IMAGE PROCESSING APPARATUS, IMAGE PROCESSING METHOD, AND STORAGE MEDIUM

BACKGROUND OF THE DISCLOSURE

Field of the Disclosure

The aspect of the embodiments relates to an image processing apparatus, an image processing method, and a storage medium.

Description of the Related Art

An optical coherence tomographic apparatus has been known as an ophthalmologic imaging apparatus for capturing an image of a subject's eye. The optical coherence tomographic apparatus obtains cross-sectional images and three-dimensional images of a fundus and an anterior eye portion using optical coherence tomography (OCT). Furthermore, the data obtained by the optical coherence tomographic apparatus is used for analysis processing for recognizing the state of the subject's eye.

The analysis processing includes the analysis of the thickness of a layer tissue of a fundus (fundus layer thickness analysis). In the fundus layer thickness analysis, the generation of a thickness distribution of a predetermined layer tissue, and comparison with a normal eye database are performed. Targeted layer tissues include a retinal nerve fiber layer (RNFL), a ganglion cell layer (GCL), a composite layer of the GCL and an inner plexiform layer (IPL), and a composite layer of the GCL, the IPL, and the RNFL.

In some cases, analysis processing is performed over a wide range. In the fundus layer thickness analysis regarding glaucoma, both of a region including an optic disk (optive nerve head portion) and a region including a macular area are targeted. In the prior art, data collection of the region including an optic disk and data collection of the region including a macular area are individually performed, and the collected data is individually analyzed.

Japanese Patent Application Laid-Open No. 2017-074325 discusses a technique of capturing an image of a region including an optic disk and a macular area as a widespread region of a fundus using the OCT. Japanese Patent Application Laid-Open No. 2017-074325 also discusses a technique of displaying an analysis map for an optic disk and an analysis map for a macular area that are obtained by individually analyzing a region including the optic disk and a region including the macular area, in a superimposed manner on a front image of a subject's eye, for easily recognizing the state over the widespread region of the fundus. At this time, Japanese Patent Application Laid-Open No. 2017-074325 discusses that the analysis map for the optic disk and the analysis map for the macular area are displayed with partially overlapping each other.

SUMMARY OF THE DISCLOSURE

According to an aspect of the embodiments, an apparatus includes an obtaining unit configured to obtain, using a coherence tomography, an analysis map for an disk and an analysis map for a macular area, which are analysis results of three-dimensional data obtained by capturing an image of a region of a fundus of a subject's eye that includes the disk and the macular area, and a control unit configured to cause a display unit to display side by side a two-dimensional image of the region including the disk and the macular area, the analysis map for the optic disk, and the analysis map for the macular area.

Further features of the disclosure will become apparent from the following description of exemplary embodiments with reference to the attached drawings.

BRIEF DESCRIPTION OF THE DRAWINGS

FIGS. 5A and 5B are diagrams each illustrating a screen displaying an image.

FIG. 6 is a diagram illustrating a screen displaying an image.

FIGS. 8A and 8B are diagrams each illustrating a screen displaying an image.

FIG. 9 is a flowchart illustrating a flow of time-series data selection.

FIG. 11 is a diagram illustrating a screen displaying an image.

FIG. 14 is a diagram illustrating a screen displaying an image.

DESCRIPTION OF THE EMBODIMENTS

Figure 1:
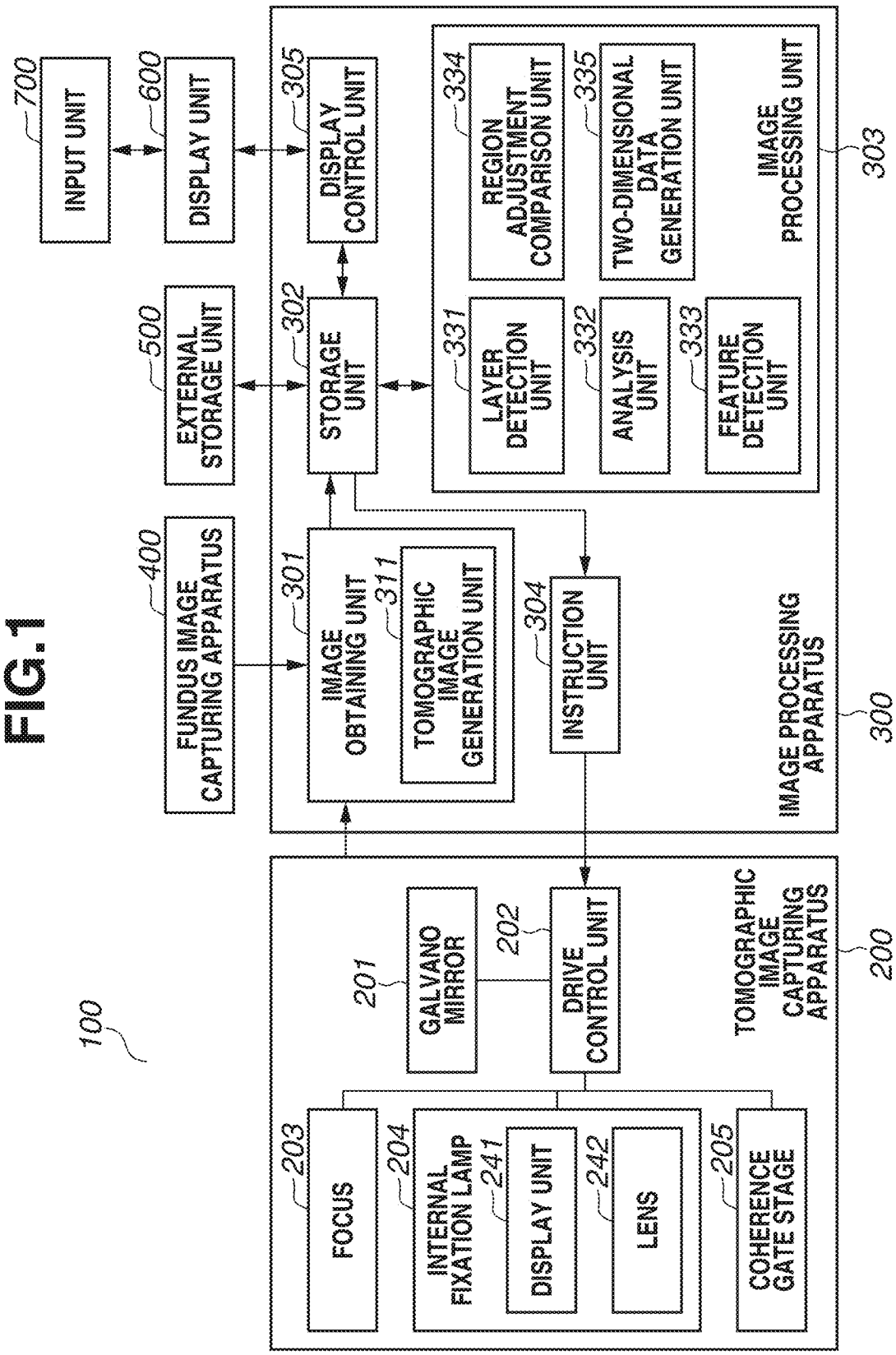
FIG. 1 is a block diagram illustrating a configuration of an image processing system.

Hereinafter, a first exemplary embodiment will be described with reference to the drawings. In a region in which an analysis map for an optic disk (optive nerve head portion) and an analysis map for a macular area partially overlap each other, a part of an analysis map located upside covers a part of an analysis map located on the bottom side. The part of the analysis map located on the bottom side accordingly becomes invisible, which lowers convenience for an examiner making a diagnosis. As one object, the present exemplary embodiment aims to enhance convenience for an examiner making a diagnosis. Thus, according to an aspect of the present exemplary embodiment, the analysis of a region including an optic disk and the analysis of a region including a macular area (fovea) are performed on a single piece of three-dimensional data of a fundus obtained by one scan pattern (e.g., raster scan) using an optical coherence tomography (OCT), and results (analysis maps) obtained by the analyses are displayed side by side on a display unit. In other words, according to an aspect of the present exemplary embodiment, an analysis map for an optic disk and an analysis map for a macular area, which are analysis results of three-dimensional data obtained by capturing an image of a region including an optic disk and a macular area of a fundus of a subject's eye, are obtained using the OCT, and these analysis maps are displayed side by side on the display unit. At this time, according to an aspect of the present exemplary embodiment, these analysis maps and the two-dimensional image of the region including the optic disk and the macular area are displayed side by side on the display unit. This can enhance convenience for an examiner making a diagnoses. This is because such display can prevent a situation caused by the prior art, such as a situation in which a part of one analysis map becomes invisible by an analysis map for an optic disk and an analysis map for a macular area partially overlapping each other, for example.

The analysis map for an optic disk may be any two-dimensional image as long as the two-dimensional image indicates an analysis result of a region including the optic disk. In addition, the analysis map for a macular area may be any two-dimensional image as long as the two-dimensional image indicates an analysis result of a region including the macular area. The two-dimensional image indicating an analysis result is, for example, a layer thickness map to be described below, a vascular density map, and a map indicating a comparison result between analysis information (e.g., layer thickness information) obtained by performing analysis and statistical information (normative data) of normal eyes.

The two-dimensional image of a region including an optic disk and a macular area is a scanning laser ophthalmoscope (SLO) image (or a color fundus image or a monochrome fundus image) obtained by capturing an image of the region including the optic disk and the macular area, for example. In addition, the two-dimensional image of a region including an optic disk and a macular area is three-dimensional data obtained using the OCT, for example, and is a front image (Enface image) obtained using at least partial data of three-dimensional data in a depth direction of a subject's eye. In addition, the two-dimensional image of a region including an optic disk and a macular area is, for example, a layer thickness map obtained by superimposing, on the above-described front image, layer thickness information (with a predetermined transparency being set) obtained by analyzing at least partial data of three-dimensional data in the depth direction of a subject's eye as color information.

According to another aspect of the present exemplary embodiment, a two-dimensional image of a region including an optic disk and a macular area, and one analysis map of an analysis map for an optic disk and an analysis map for a macular area may be displayed on the display unit in an overlapping manner. At this time, according to another aspect of the present exemplary embodiment, the other analysis map and the two-dimensional image may be displayed side by side on the display unit. In this way, for example, the analysis map for the optic disk and the analysis map for the macular area can be displayed without partially overlapping each other. This can enhance convenience for an examiner making a diagnoses. At this time, an analysis map to be displayed to overlap the two-dimensional image may be displayed to overlap at a corresponding position on the two-dimensional image. In addition, the other analysis map may be displayed on the display unit to overlap another two-dimensional image. At this time, the two two-dimensional images on which the analysis maps are displayed in an overlapping manner may be two-dimensional images of the same type, or may be two-dimensional images of different types.

Hereinafter, an image processing system including an image processing apparatus according to the present exemplary embodiment will be described in detail.

FIG. 1 is a block diagram illustrating a configuration of an image processing system 100 including an image processing apparatus 300 according to the present exemplary embodiment. As illustrated in FIG. 1, the image processing system 100 has a configuration in which the image processing apparatus 300 is connected with a tomographic image capturing apparatus 200, a fundus image capturing apparatus 400, an external storage unit 500, a display unit 600, and an input unit 700 via interfaces.

The tomographic image capturing apparatus 200 is an apparatus that captures a tomographic image of an eye portion. The tomographic image capturing apparatus 200 uses an optical coherence tomography (OCT) such as a Spectral domain OCT (SD-OCT) or a Swept Source OCT (SS-OCT), for example. The SD-OCT is an OCT that obtains an interferogram by a spectroscope using a broadband light source. In addition, the SS-OCT is an OCT that measures spectral interference by a single-channel light detector by using a high-speed wavelength sweep light source as a light source. At this time, the tomographic image capturing apparatus 200 is an example of an ophthalmologic imaging apparatus including a detection unit (not illustrated) that detects interfering light of return light from a fundus irradiated with measurement light, and reference light, and the OCT. Because the tomographic image capturing apparatus 200 is a known apparatus, the detailed description will be omitted. The description will be given of the image capturing of a tomographic image and analysis processing, which are to be performed in response to an instruction from the image processing apparatus 300.

In FIG. 1, a galvano mirror 201 is provided for scanning a fundus with measurement light, and defines an imaging range of a fundus to be targeted by the OCT apparatus. In addition, by controlling a drive range and a speed of the galvano mirror 201, a drive control unit 202 defines an imaging range in a planar direction of the fundus and the number of scanning lines (scanning speed in the planar direction). For the sake of simplicity, FIG. 1 illustrates the galvano mirror 201 as one unit. Actually, the galvano mirror 201 includes a mirror for X scan and a mirror for Y scan, and a desired range on the fundus can be scanned with measurement light.

A focus 203 is provided for performing focusing on a retinal layer of the fundus via an anterior eye portion of an eye (subject). By a focus lens (not illustrated), measurement light is focused on the retinal layer of the fundus via the anterior eye portion of the eye (subject). The measurement light emitted onto the fundus returns after being reflected and scattered by each retinal layer.

An internal fixation lamp 204 includes a display unit 241 and a lens 242. A display unit in which a plurality of light-emitting diodes (LEDs) is arranged in a matrix is used as the display unit 241. A turning-on position of a light-emitting diode is changed based on a region desired to be targeted for image capturing, by the control of the drive control unit 202. The positions of a fixation lamp include a macular area fixation lamp position for capturing an image of a macular area periphery, an optic disk fixation lamp position for capturing an image of an optic disk periphery, and a posterior fundus center fixation lamp position for capturing an image including both of the macular area and the optic disk. Light from the display unit 241 is guided to a subject's eye via the lens 242. The wavelength of light emitted from the display unit 241 is 520 nm, and a desired pattern is displayed by the drive control unit 202.

A coherence gate stage 205 is controlled by the drive control unit 202 to deal with a difference in eye axial length of a subject's eye. A coherence gate indicates a position at which optical distances of measurement light and reference light in the OCT become equal. Furthermore, by controlling the position of the coherence gate as an image capturing method, a position of image capturing is controlled. For example, whether to capture an image of a retinal layer side or capture an image of a deep side of a retinal layer is controlled. The structure of an eye and an image of the eye to be obtained by the image processing system 100 will be described with reference to FIG. 2.

Figure 2A:
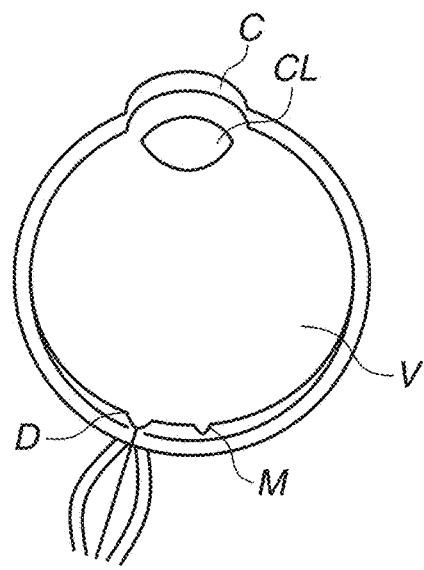
FIGS. 2A, 2B, and 2C are diagrams illustrating a structure of an eye portion, a tomographic image, and a fundus image.

FIG. 2A is a schematic diagram of an eye ball. In FIG. 2A, the eye ball includes a cornea C, a crystalline lens CL, a vitreum V, a macular area M (central part of a macula indicates a fovea), and an optic disk D. The description will be given of a case where the tomographic image capturing apparatus 200 according to the present exemplary embodiment mainly captures an image of a posterior fundus of a retina including the vitreum V, the macular area M, and the optic disk D. The tomographic image capturing apparatus 200 can also capture an image of an anterior eye portion including the cornea C and the crystalline lens CL.

Figure 2B:
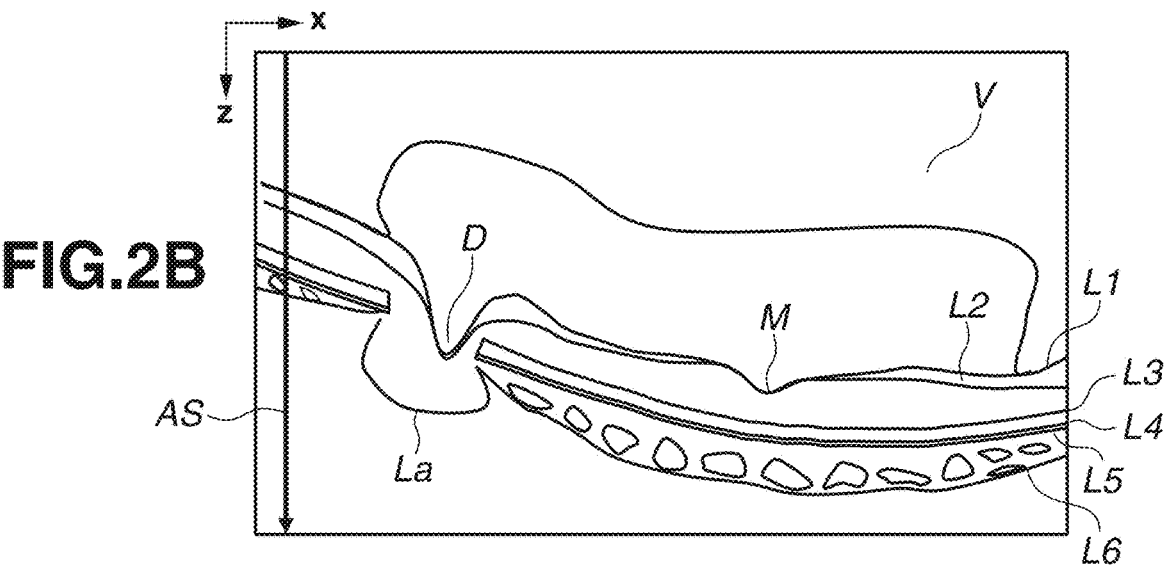

FIG. 2B illustrates an example of a tomographic image to be obtained by the tomographic image capturing apparatus 200 in a case where the tomographic image capturing apparatus 200 captures an image of a retina. In FIG. 2B, "AS" indicates a unit of image obtaining in an OCT tomographic image called an A scan. A plurality of A scans constitute one B scan. In addition, the B scan will be referred to as a tomographic image. The tomographic image in FIG. 2B includes the vitreum V, the macular area M, and the optic disk D, and a cribrosa lamina La. Further, L1 denotes a boundary between an inner limiting membrane (ILM) and a nerve fiber layer (NFL), L2 denotes a boundary between the NFL and a ganglion cell layer (GCL), L3 denotes an inner segment outer segment junction (ISOS) of a photoreceptor cell, L4 denotes a retinal pigment epithelium layer (RPE), L5 denotes a Bruch membrane (BM), and L6 denotes a choroid membrane. In the tomographic image, a horizontal axis (main scanning direction of OCT) is defined as an x-axis and a vertical axis (depth direction) is defined as a z-axis.

Figure 2C:
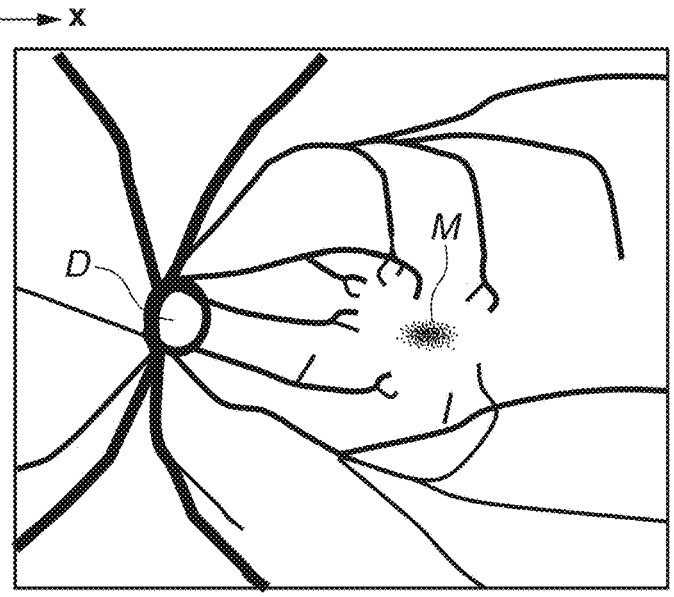

FIG. 2C illustrates an example of a fundus image to be obtained by the fundus image capturing apparatus 400. The fundus image capturing apparatus 400 is an apparatus that captures a fundus image of an eye portion. Examples of the apparatus include a fundus camera and an SLO. The fundus image in FIG. 2C includes the macular area M and the optic disk D. In FIG. 2C, thick curves indicate blood vessels of a retina. In the fundus image, a horizontal axis (main scanning direction of OCT) is defined as the x-axis, and a vertical axis (sub-scanning direction of OCT) is defined as a y-axis. An apparatus configuration of the tomographic image capturing apparatus 200 and the fundus image capturing apparatus 400 may be an integrated configuration or may be a separated configuration.

The image processing apparatus 300 includes an image obtaining unit 301, a storage unit 302, an image processing unit 303, an instruction unit 304, and a display control unit 305. The image obtaining unit 301 includes a tomographic image generation unit 311, and generates a tomographic image by obtaining signal data of a tomographic image captured by the tomographic image capturing apparatus 200, and performing signal processing. In addition, the image obtaining unit 301 obtains fundus image data captured by the fundus image capturing apparatus 400. Then, the generated tomographic image and the fundus image are stored into the storage unit 302. The image processing unit 303 includes a layer detection unit 331, an analysis unit 332, a feature detection unit 333, a region adjustment comparison unit 334, and a two-dimensional data generation unit 335.

The layer detection unit 331 detects a boundary line of each layer from a tomographic image. The analysis unit 332 calculates the thickness of each layer based on boundary line information detected by the layer detection unit 331. The feature detection unit 333 detects an optic disk or a macular area central fovea using at least one of a tomographic image or a fundus image. Based on a position of a region detected by the feature detection unit 333, the region adjustment comparison unit 334 adjusts a position and a size of a region to be compared with normative data (statistical value calculated from a plurality of pieces of data) to be described below, and then performs data comparison. The two-dimensional data generation unit 335 generates two-dimensional data based on an analysis result by the analysis unit 332 and a comparison result by the region adjustment comparison unit 334.

The external storage unit 500 stores information regarding a subject's eye (name, age, and gender of patient), captured image data, an image capturing parameter, an image analysis parameter, and a parameter set by an operator, in association with each other. The external storage unit 500 further stores normative data generated from information regarding a plurality of normal eyes. For example, the normative data includes the thickness of the NFL near the optic disk, and the thickness of a composite layer of the NFL, the GCL, and the IPL near the macular area central fovea.

Examples of the input unit 700 include a mouse, a keyboard, and a touch-operated screen, and an operator issues instructions to the image processing apparatus 300, the tomographic image capturing apparatus 200, and the fundus image capturing apparatus 400 via the input unit 700.

Figure 3:
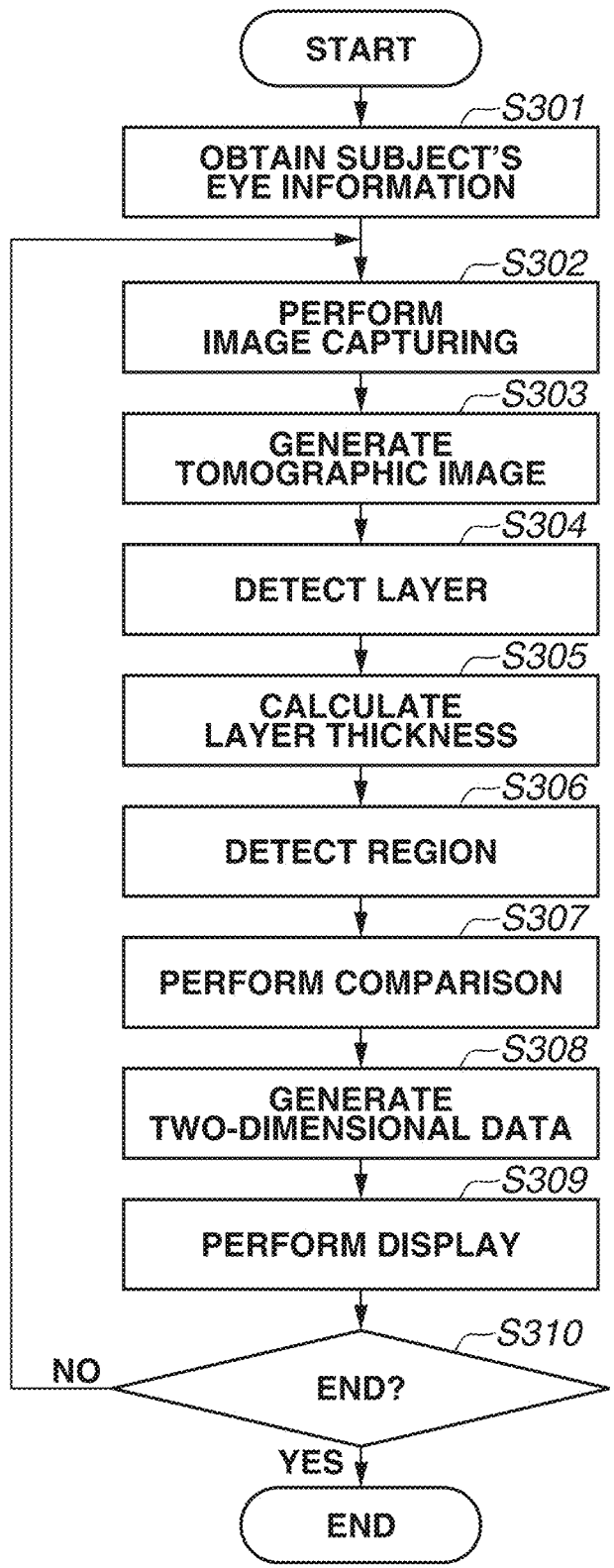
FIG. 3 is a flowchart illustrating a flow of processing in the image processing system.

Next, a processing procedure of the image processing apparatus 300 according to the present exemplary embodiment will be described with reference to FIG. 3. FIG. 3 is a flowchart illustrating operation processing of the entire system according to the present exemplary embodiment.

In step S301, a subject's eye information obtaining unit (not illustrated) obtains a subject identification number from the outside as information for identifying a subject's eye. Then, based on the subject identification number, the subject's eye information obtaining unit obtains information regarding the subject's eye that is stored in the external storage unit 500, and stores the information into the storage unit 302.

In step S302, image capturing is performed by scanning a subject's eye. A subject's eye is scanned in the following manner. If an operator selects a scan start (not illustrated), the tomographic image capturing apparatus 200 controls the drive control unit 202 to operate the galvano mirror 201, and a tomographic image target is scanned. The galvano mirror 201 includes an X scanner for a horizontal direction and the Y scanner for a vertical direction. Thus, by individually changing the directions of these scanners, scanning can be performed in both directions of the horizontal direction (X) and the vertical direction (Y) in an apparatus coordinate system. Then, by simultaneously changing the directions of these scanners, scanning can be performed in a combined direction of the horizontal direction and the vertical direction. Thus, scanning can be performed in an arbitrary direction on a fundus plane.

For performing image capturing, various image capturing parameters are adjusted. More specifically, at least the position of the internal fixation lamp, a scan range, a scan pattern, a coherence gate position, and a focus are set. The drive control unit 202 controls the light-emitting diodes of the display unit 241, and controls the position of the internal fixation lamp 204 so as to capture an image centered on a posterior eye, a macular area, or an optive nerve head. As a scan pattern, a scan pattern such as raster scan for capturing a three-dimensional volume image, radial scan, or cross scan is set. In the present exemplary embodiment, the description will be given of a case where wide area (broad area) image capturing is performed by setting the position of the fixation lamp at the posterior eye center, using the raster scan as a scan pattern, and using a scan range covering the entire region from the optic disk to the macular area. In the present exemplary embodiment, for example, a scan range is set to a range of 13×10 mm, and raster scan in which the main scanning direction corresponds to the vertical direction is performed. Furthermore, an image of an imaging range center is captured by horizontal scanning By the horizontal scanning, image capturing is performed before or after three-dimensional raster scan. By the horizontal scanning, one or a plurality of images (e.g., about ten images) are captured. Image capturing is performed by an operator selecting an image capturing start (not illustrated) after ending adjustment of these image capturing parameters. The tomographic image capturing apparatus 200 can also perform tracking of a subject's eye. With this configuration, good-condition three-dimensional data can be obtained by suppressing the influence of an involuntary eye movement, and performing rescan only at a location of defective data in a case where data includes a defect caused by blinking.

In step S303, a tomographic image is generated. The tomographic image generation unit 311 generates a tomographic image by performing general reconstruction processing on each interference signal.

First of all, the tomographic image generation unit 311 performs fixed pattern noise removal from an interference signal. The fixed pattern noise removal is performed by extracting a fixed pattern noise by averaging a plurality of detected A scan signals, and subtracting the fixed pattern noise from an input interference signal. Next, the tomographic image generation unit 311 performs desired window function processing for optimizing a depth resolution and a dynamic range that are in a trade-off relationship in a case where Fourier transform is performed at a finite interval. Next, fast Fourier transform (FFT) processing is performed, and a tomographic signal is thereby generated.

In step S304, the layer detection unit 331 performs layer detection. The layer detection unit 331 performs noise removal and edge enhancement processing on a processing target tomographic image. For example, a median filter or a Gaussian filter is applied as noise removal processing. A Sobel filter or a Hessian filter is applied as edge enhancement processing. Edge enhancement processing on a two-dimensional tomographic image will be described using a two-dimensional Hessian filter. The Hessian filter can enhance a secondary local structure of a two-dimensional tone distribution based on a relationship between two eigen values ($\lambda_1, \lambda_2$) of a Hessian matrix. A two-dimensional line structure is enhanced using a relationship between eigen values and eigenvector ($e_1, e_2$) of the Hessian matrix. Because a line structure in a two-dimensional tomographic image corresponds to a retinal layer, a structure of the retinal layer is enhanced. Retinal layers having different thicknesses can be detected by changing resolution of smoothing to be performed using a gauss function when a Hessian matrix is calculated. When a two-dimensional Hessian filter is applied, the two-dimensional Hessian filter is applied after data is deformed so as to equalize physical sizes in X and Z directions of an image. In a case of a general OCT, physical sizes in the X and Y directions and the Z direction are different. Thus, a filter is applied after matching the physical sizes of a retinal layer for each pixel. Alternatively, when physical sizes are not normalized, adjustment can also be approximately performed by changing resolution of smoothing to be performed using a gauss function. The above description has been given of the processing of a two-dimensional tomographic image, but the processing is not limited to this. When a data structure used when a tomographic image is captured is a three-dimensional tomographic image obtained by raster scan, a three-dimensional Hessian filter can also be applied. In this case, after positioning processing is performed in the X and Z directions on adjacent tomographic images by a positioning unit (not illustrated), a secondary local structure of a three-dimensional tone distribution can be enhanced based on a relationship between three eigen values ($\lambda_1, \lambda_2, \lambda_3$) of a Hessian matrix. By enhancing a three-dimensional layer structure using a relationship between eigen values and eigenvector ($e_1, e_2, e_3$) of the Hessian matrix, an edge can also be enhanced three-dimensionally.

The layer detection unit 331 detects a boundary line from a tomographic image having been subjected to edge enhancement processing. In the present exemplary embodiment, a boundary between the ILM and the NFL, and the RPE are initially obtained, and the ISOS, and the boundary between the NFL and the GCL are subsequently detected. As another boundary line, a boundary between an outer plexiform layer (OPL) and an outer nuclear layer (ONL), a boundary between an inner plexiform layer (IPL) and an inner nuclear layer (INL), a boundary between the INL and the OPL, a boundary between the GCL and the IPL, and a boundary between a choroid membrane and a sclera, which are not illustrated, may be detected. As a detection method of a boundary, processing of detecting a plurality of points having higher edge intensity, from each A scan, as boundary candidates, and connecting the points as a line based on continuity between boundary candidates in neighboring A scans is performed. When points are connected as a line, by evaluating the smoothness of the line, outliers are removed. Then, a boundary line is determined based on distances from upper and lower boundary lines, and a positional relationship. If no boundary line is detected as a result of removal of outliers from each A scan, a boundary line may be obtained by performing interpolation from nearby boundary lines. Alternatively, nearby boundary lines may be searched for a boundary line candidate in the horizontal direction based on an edge, and a boundary line may be determined again based on the boundary line candidate discovered from the nearby boundary lines.

Then, processing of correcting a shape of a boundary line into a smooth shape is executed on the detected boundary line. For example, the shape of the boundary line may be smoothened using an image feature and a shape feature by Snakes. Alternatively, by regarding coordinate values of the boundary line shape as time-series data obtained by signals, the shape may be smoothened by Savitzky-Golay filter or smoothing processing such as simple moving average, weighted moving average, or exponential moving average. Alternatively, instead of detecting boundary lines for all A scans, boundary lines may be discretely (e.g., every five A scans) detected, and boundary line positions of A scans from which boundary lines are not detected may be obtained from the detected boundary lines by interpolation.

In step S305, the analysis unit 332 calculates the thickness of an arbitrary layer based on a detection result of the layer detection unit 331. For example, in a case of the thickness of the NFL, in FIG. 2B, a difference in the depth direction of a region defined by the boundary lines L1 and L2 is the thickness of the layer. The layer is not limited to the NFL, and the thickness of a composite layer of the NFL, the GCL, and the IPL may be calculated, or a thickness of all layers including the NFL (or ILM) to the BM (or RPE) may be calculated. Because a calculated result is a value of one point for each A scan, thicknesses are calculated from all A scans and B scans, and a two-dimensional layer thickness map is obtained. If there is a plurality of types of calculation target layers, a plurality of two-dimensional layer thickness maps is output.

In step S306, the feature detection unit 333 detects an optic disk and a macular area central fovea. First of all, an example of detection of an optic disk will be described. The feature detection unit 333 uniformizes the brightness of an image to a certain standard by adjusting contrast of an Enface image (retina front image) generated from an SLO image or a plurality of OCT tomographic images. Then, the image is smoothened using a smoothing filter such as a Gaussian filter or a median filter. Furthermore, for enhancing the feature of the image, contrast may be enhanced by performing processing such as Contrast Limited Adaptive Histogram Equalization (CLAHE). Because a circular (ellipsoidal) region with a low brightness value can be extracted from the image by performing these types of preprocessing, the extracted region is defined as an optic disk. Furthermore, a layer boundary line detection result in an OCT tomographic image may be used in addition to a retina front image such as an SLO image or an Enface image. For example, as indicated as the optic disk D in FIG. 2B, the optic disk is a large depressed region. Thus, an optic disk may be extracted based on a shape feature obtained from a detection result of a layer boundary line.

Next, an example of detection of a macular area central fovea will be described. As indicated as the macular area M in FIG. 2B, a macular area central fovea is a small depressed region. Furthermore, a distance between the ILM and an IS/OS becomes smaller as compared with other locations. Thus, by using a distance between the ILM and the IS/OS, a depressed region of the macular area central fovea can be obtained. Because no IS/OS exists in the optic disk although the optic disk is a depressed region similarly, a feature detected using a distance between an ILM and an IS/OS in the optic disk becomes an invalid region.

Detection examples of a layer boundary and a feature portion using image processing have been described with reference to steps S304 and S306, but detection is not limited to this. By learning images and correct labels using a machine learning method such as deep learning, an arbitrary layer or feature portion may be detected from an input image.

In step S307, the region adjustment comparison unit 334 performs adjustment of a region to be compared with normative data, based on the positions of the optic disk and the macular area extracted by the feature detection unit 333. The adjustment will be described with reference to FIGS. 4A, 4B, and 4C. The description will be given assuming that normative data of the present exemplary embodiment separately stores data of an optic disk periphery and data of a macular area periphery.

Figure 4A:
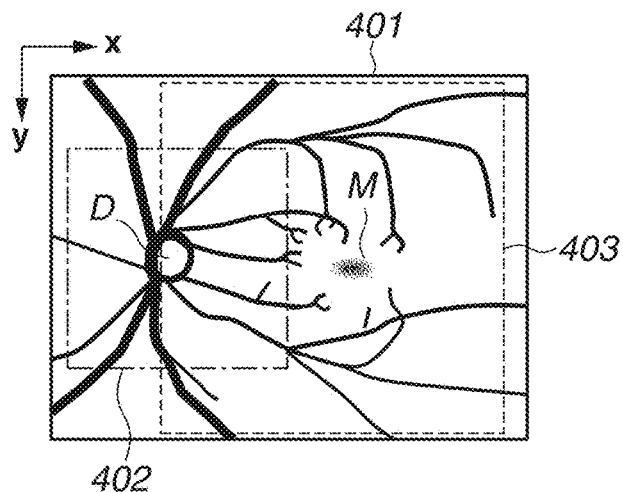
FIGS. 4A, 4B, and 4C are diagrams illustrating an image capturing region.
Figure 4B:
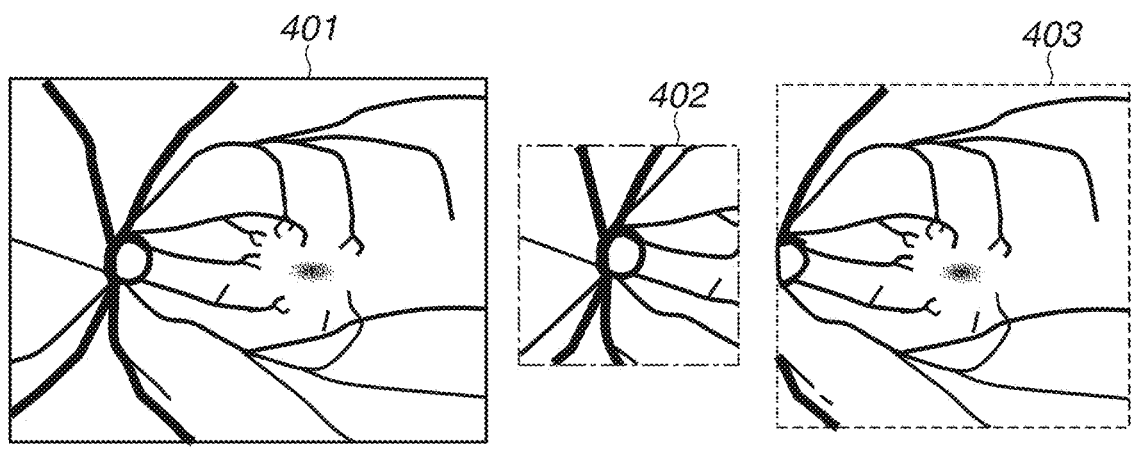
Figure 4C:
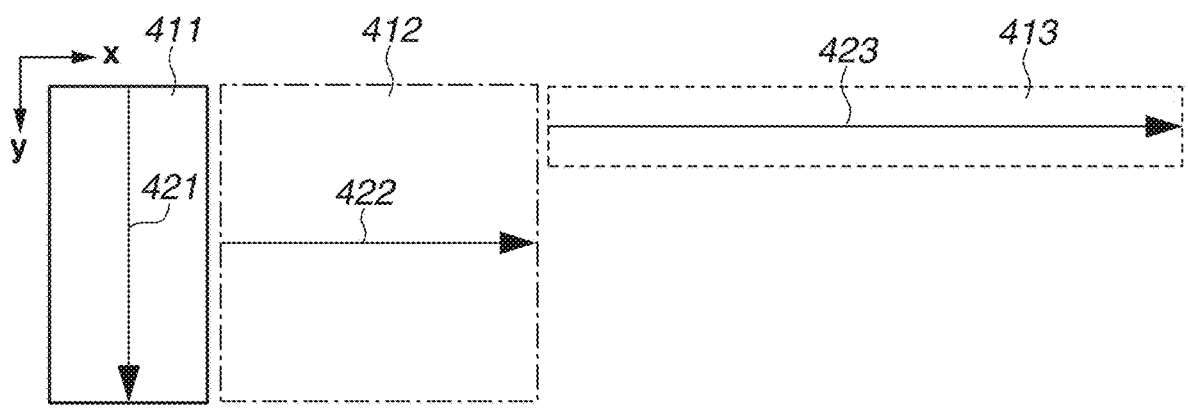

A rectangular region 401 indicated by a solid line in FIG. 4A is an example of a wide-area image capturing region covering the entire region from an optic disk to a macular area in the present exemplary embodiment. For example, in the present exemplary embodiment, the rectangular region 401 is a range of 13×10 mm A rectangular region 402 indicated by a dashed-dotted line indicates a range of normative data in the optic disk, and is a range of 6×6 mm, for example. A rectangular region 403 indicated by a dotted line indicates a range of normative data in the macular area, and is a range of 10×10 mm, for example. FIG. 4B separately illustrates regions overlapping in FIG. 4A. FIGS. 4A and 4B illustrate examples in which regions are represented by size, but in the case of OCT, resolution varies depending on the number of A scans and the number of B scans used for capturing an image of a certain range. FIG. 4C illustrates this situation. In FIG. 4C, for the sake of explanation, features of the optic disk, the macular area, and blood vessels are omitted, and only a ratio between an A scan and a B scan is illustrated. In FIG. 4C, a rectangular region 411 indicates a size representing a ratio between an A scan and a B scan corresponding to the rectangular region 401, and an arrow 421 indicates a main scanning direction. In the present exemplary embodiment, the rectangular region 411 is an example indicating a size of 500 A scans and 250 B scans. In a similar manner, a rectangular region 412 corresponds to the rectangular region 402 and a rectangular region 413 corresponds to the rectangular region 403, and each indicates a size representing a ratio between an A scan and a B scan. The rectangular region 412 is an example indicating a size of 500 A scans and 500 B scans, and the rectangular region 413 is an example indicating a size of 1000 A scans and 125 B scans.

As illustrated in FIGS. 4A, 4B, and 4C, even if an imaging range set at the time of wide-area image capturing covers an imaging range set at the time of normative data obtaining, a resolution set at the time of image capturing and a resolution set at the time of normative data obtaining are different in some cases. Thus, the region adjustment comparison unit 334 performs adjustment of a layer thickness map region obtained in step S305. An example of region adjustment will be described. The region adjustment comparison unit 334 performs expansion/reduction of a layer thickness map corresponding to the rectangular region 411, into a ratio of 13:10 in such a manner that the layer thickness map corresponds to an image capturing region. A layer thickness map corresponding to the rectangular region 401 as illustrated in FIG. 4B is thereby obtained. Because the layer thickness map is a two-dimensional layer thickness map, a method of expansion/reduction may be general image processing such as Bicubic and Bilinear, or super-resolution processing preliminarily learned by machine learning may be applied. From the expanded or reduced layer thickness map, a range with a ratio of 6:6 with, as a center, a point corresponding to the position of the optic disk extracted by the feature detection unit 333 in step S306, and a range with a ratio of 10:10 with, as a center, a point corresponding to the position of the macular area extracted similarly, are identified. Expansion/reduction is also performed on normative data corresponding to the optic disk and the macular area with ratios of 6:6 and 10:10, respectively, and the normative data is compared with the layer thickness map.

An example has been described above in which simple expansion/reduction is performed irrespective of the numbers of A scans and B scans at the time of image capturing, but expansion/reduction is not limited to this. For example, expansion/reduction may be performed after data having high resolution at the time of data obtaining are thinned out. For example, the rectangular region 412 indicates an example in which normative data is generated by obtaining data of 500×500 as a range of 6×6 mm After the data are thinned out to be adapted to the rectangular region 411 of the present exemplary embodiment, expansion/reduction may be performed. For example, by executing expansion/reduction processing after data of 500×500 are thinned out to become data of 115×300, almost the same scale conversion as the expansion/reduction of the rectangular region 411 can be performed, and almost the same interpolation processing as the interpolation processing by the expansion/reduction can be performed. Thus, even if a resolution set at the time of image capturing and a resolution set at the time of normative data obtaining are different, resolutions set at the time of data comparison can be set to almost the same resolution.

The region adjustment comparison unit 334 is an example of an adjustment unit that adjusts the numbers of A scans and B scans in three-dimensional data by adjusting a position and a size of a partial region in three-dimensional data to be compared with statistical information of normal eyes, based on the position of the optic disk or the macular area in the three-dimensional data.

In the present exemplary embodiment, the description has been given of a processing flow of creating a layer thickness map in step S305, and identifying comparison ranges with, as respective centers, points corresponding to the optic disk and the macular area in step S307, but a processing flow is not limited to this. For example, after comparison ranges with points corresponding to the optic disk and the macular area, as respective centers, are identified from a fundus front image, a layer thickness map may be created based on boundary line data included in the ranges.

In step S308, the two-dimensional data generation unit 335 generates two-dimensional data (also referred to as an analysis map) of an optic disk periphery and a macular area central fovea periphery that have been compared with normative data by the region adjustment comparison unit 334. In the present exemplary embodiment, analysis maps generated by the two-dimensional data generation unit 335 are a Significance map or a Deviation map. The Significance map is a map in which a display color of each measurement value is varied based on normative data assuming that measurement values smaller than 1 percentile of a confidential interval fall within an abnormal range, measurement values smaller than 5 percentile fall within a boundary range, and the remaining values fall within a normal range. The Deviation map is a map in which a difference from an average image of a layer thickness map calculated from normative data is represented by color. The layer thickness map has already been created by the analysis unit 332 when a layer thickness has been calculated.

The two-dimensional data generation unit 335 generates, for example, a Significance map and a Deviation map of the NFL in the optic disk periphery. In addition, in the macular area central fovea periphery, the two-dimensional data generation unit 335 generates a Significance map and a Deviation map of a composite layer of the NFL, the GCL, and the IPL, or all layers including all layers from the NFL (or ILM) to the BM (or RPE). The Significance map and the Deviation map are examples of a two-dimensional image (analysis map) indicating an analysis result.

An analysis map for an optic disk may be a first comparison map indicating a comparison result of layer thickness information regarding an optic disk obtained by analyzing three-dimensional data, and statistical information (normative data) of normal eyes regarding an optic disk. In addition, an analysis map for a macular area may be a second comparison map indicating a comparison result of layer thickness information regarding a macular area obtained by analyzing three-dimensional data, and statistical information (normative data) of normal eyes regarding a macular area. At this time, a Significance map and a Deviation map are examples of the first comparison map and the second comparison map.

The two-dimensional data generation unit 335 is an example of an obtaining unit that obtains an analysis map for an optic disk and an analysis map for a macular area, which are analysis results of three-dimensional data obtained by capturing an image of a region of a fundus of a subject's eye that includes an optic disk and a macular area, using an OCT. At this time, the obtaining unit can generate an analysis map for an optic disk and an analysis map for a macular area by analyzing the above-described three-dimensional data. The obtaining unit may be configured to obtain an analysis map for an optic disk and an analysis map for a macular area as data from an external storage unit or an external system by wired or wireless communication.

In step S309, a captured image, a layer thickness map, and an analysis map are displayed on the display unit 600. FIGS. 5A and 5B each illustrate an example of a screen to be displayed on the display unit 600. FIGS. 5A and 5B illustrate an entire screen 505, a patient tab 501, an image capturing tab 502, a report tab 503, and a setting tab 504. Diagonal hatches of the report tab 503 indicates an active state of a report screen. In the present exemplary embodiment, the description will be given of an example in which the report screen is displayed. FIGS. 5A and 5B illustrate display examples of two types of report screens. In the present exemplary embodiment, by performing wide-area scan, an image covering an optic disk and a macular area is captured. Thus, for example, FIG. 5A illustrates a report example, for example, for glaucoma diagnosis in a layout centered on an optic disk. FIG. 5B illustrates a report example for macular disease diagnosis in a layout centered on a macular area. These layouts are just examples, and the number of types is not limited to two. A plurality of layouts suitable for intended purposes can be selected from one scan pattern.

In FIG. 5A, an image 510 illustrates a fundus image, and an image 511 is an enlarged image of an optic disk periphery extracted from the fundus photograph. In a case where the fundus image 510 is not captured, another image captured as a fundus front image such as an SLO image or an infrared image is displayed. A map 512 is a layer thickness map indicating the thickness of the entire retina, and is an example of a two-dimensional image of a region including an optic disk and a macular area. A grid 513 is an Early Treatment Diabetic Retinopathy Study (ETDRS) grid displayed in a superimposed manner on the layer thickness map of the entire retina. The ETDRS grid 513 displays an average value of thicknesses of the entire retina within the region in each sector. A map 514 is a layer thickness map indicating the thickness of the RNFL. In addition, information 515 indicating a range (e.g., range of 10×10 mm) of a macular area periphery is an example of information indicating a position of an analysis map for a macular area in the above-described two-dimensional image. The layer thickness map 514 is only required to be either one layer thickness map of a layer thickness map indicating the thickness of the RNFL, and a layer thickness map indicating the thickness of a composite layer of the NFL, the GCL, and the IPL (or the thickness of a composite layer of the GCL and the IPL). These layer thickness maps may be displayed to be switchable from one to another. The switching of the display may be made executable using a Split Button, for example. A button is not limited to the Split Button, and may be a Radio Button or another button that allows one of a plurality of options to be selectable. Information 516 indicating a range (e.g., range of 6×6 mm) of an optic disk periphery is an example of information indicating a position of an analysis map for an optic disk in the above-described two-dimensional image. A circle 517 indicates a circle around an optic disk, and has a diameter of 3.45 mm, for example. Maps 518 and 519 are a Significance map and a Deviation map each having a range of 6×6 mm indicated by the information 516, and are generated based on normative data as for the thickness of the RNFL. Maps 520 and 521 are a Significance map and a Deviation map each having a range of 10×10 mm indicated by the information 515, and are generated based on normative data as for the thickness of the composite layer of the NFL, the GCL, and the IPL. In the layer thickness maps, the Significance map, and the Deviation map, colored results are displayed in a superimposed manner on a fundus front image generated from a tomographic image in a semipermeable state (predetermined transparency) by a permeability setting.

In addition, an image 522 is a tomographic image of the circle 517, and a thickness profile 523 is a thickness profile of the RNFL in the tomographic image 522. In the thickness profile 523, a thick line indicates a measured value of the thickness of the RNFL, and thin lines indicate a normal range, a boundary range, and an abnormal range of normative data. The thickness profile 523 is displayed in TSNIT (Temporal, Superior, Nasal, Inferior), but can also be displayed in the order of NSTIN. For switching the display between TSNIT and NSTIN, for example, default display of TSNIT or NSTIN can be set on a setting screen (not illustrated). Alternatively, a menu may be displayed by right-clicking on a screen, and the display may be made switchable on the menu. A table 524 lists measurement values regarding an optic disk and the thickness of the RNFL. For example, a Disc area, a Rim area, a C/D ratio, and an average value of thicknesses of TSNIT of the RNFL are displayed. A grid 525 is a thickness grid of the RNFL in the optic disk, and a grid splitting a circle into four sectors, and a grid splitting a circle into twelve sectors are illustrated. The number of split sectors is not limited thereto, and a grid splitting a circle into six sectors may be used. In a sector split by the grid, an average value of thicknesses, and a color indicating the normal range, the boundary range, and the abnormal range within which the value falls are illustrated. A grid 526 is a thickness grid of a composite layer of the NFL, the GCL, and the IPL in a macular area. A grid vertically and horizontally splitting a circle into nine areas, the entire circle, and a grid vertically splitting the circle into two areas are illustrated. Similarly to the grid 525, in a sector split by the grid 526, an average value of thicknesses, and a color indicating the normal range, the boundary range, and the abnormal range within which the value falls are illustrated.

In FIG. 5A, the maps 520 and 521 and the grid 526 display information regarding the composite layer of the NFL, the GCL, and the IPL, but may display information regarding a composite layer of the GCL and the IPL. For switching the display between the composite layer of the NFL, the GCL, and the IPL, and the composite layer of the GCL and the IPL, default display of either layer can be set on a setting screen (not illustrated). Alternatively, a menu may be displayed by right-click on a screen, and the display may be made switchable on the menu. In the case of switching the display by right click (an example of an instruction from an examiner), if selection processing is executed on a display region of any of the maps 520 and 521 and the grid 526, the display of these three types (520, 521, 526) is switched at a synchronized timing. At this time, in a case where the layer thickness map 514 displays the thickness of not the RNFL but the composite layer of the NFL, the GCL, and the IPL, the layer thickness map 514 may be configured to be switchable in synchronization with the display of a layer thickness map indicating the thickness of the composite layer of the GCL and the IPL. More specifically, if either one layer of a layer corresponding to the layer thickness map 514 and a layer corresponding to the above-described second comparison map (520 or 521) is switched to a different layer (e.g., either layer of two types of composite layers) in response to an instruction from an examiner, the other layer may synchronously switch to the different layer. With this configuration, the display of the layer thickness map 514 and the above-described second comparison map can be changed to an analysis map corresponding to the different layer. At this time, a layer (e.g., the RNFL) corresponding to an analysis map of an optic disk may be configured not to be changed in response to the above-described instruction. Analysis maps corresponding to different layers can be thereby observed by switching a macular area and an optic disk. Thus, glaucoma diagnosis can be efficiently performed, for example. In synchronization with the display switching, the display illustrated in FIG. 5B to be described below also switches.

In FIG. 5B, a difference from FIG. 5A will be described. A horizontal scanning image 530 is a tomographic image of horizontal scanning. In the present exemplary embodiment, as described in step S302, three-dimensional image capturing and horizontal scanning are performed. By horizontal scanning, one or a plurality of image (e.g., about ten images) are captured. In the case of capturing a plurality of images, one tomographic image is generated by performing addition average processing after position alignment of a plurality of tomographic images is performed by a position alignment unit (not illustrated). Then, the tomographic image having been subjected to the addition average processing is displayed as the horizontal scanning A three-dimensionally-captured tomographic image of vertical scan may be displayed in place of the horizontal scanning, or the tomographic image of vertical scan may be displayed side by side to the horizontal scanning, which is not illustrated in FIG. 5B. A map 532 is a Significance map generated for the thickness of the entire retina based on normative data, and a map 533 is a layer thickness map indicating the thickness of the composite layer of the NFL, the GCL, and the IPL. The maps 533 and 520 display information regarding the composite layer of the NFL, the GCL, and the IPL, but this switches in synchronization with the type described with reference to FIG. 5A. More specifically, in a case where the display switches to the display of the composite layer of the GCL and the IPL on the screen in FIG. 5A, the display of two types (533, 520) in FIG. 5B displays information regarding the composite layer of the GCL and the IPL. Similar to the switching described with reference to FIG. 5A, also in FIG. 5B, the display of the layer type can be switched. In FIG. 5B, the maps 532, 520, and 518 display Significance maps, and do not display a Deviation map, but these maps can be displayed by switching. The display can be switched between a Significance map and a Deviation map by pressing a Split Button, for example. In addition, by changing any one Significance map to a Deviation map, the other Significance maps may synchronously switch.

Figure 6:
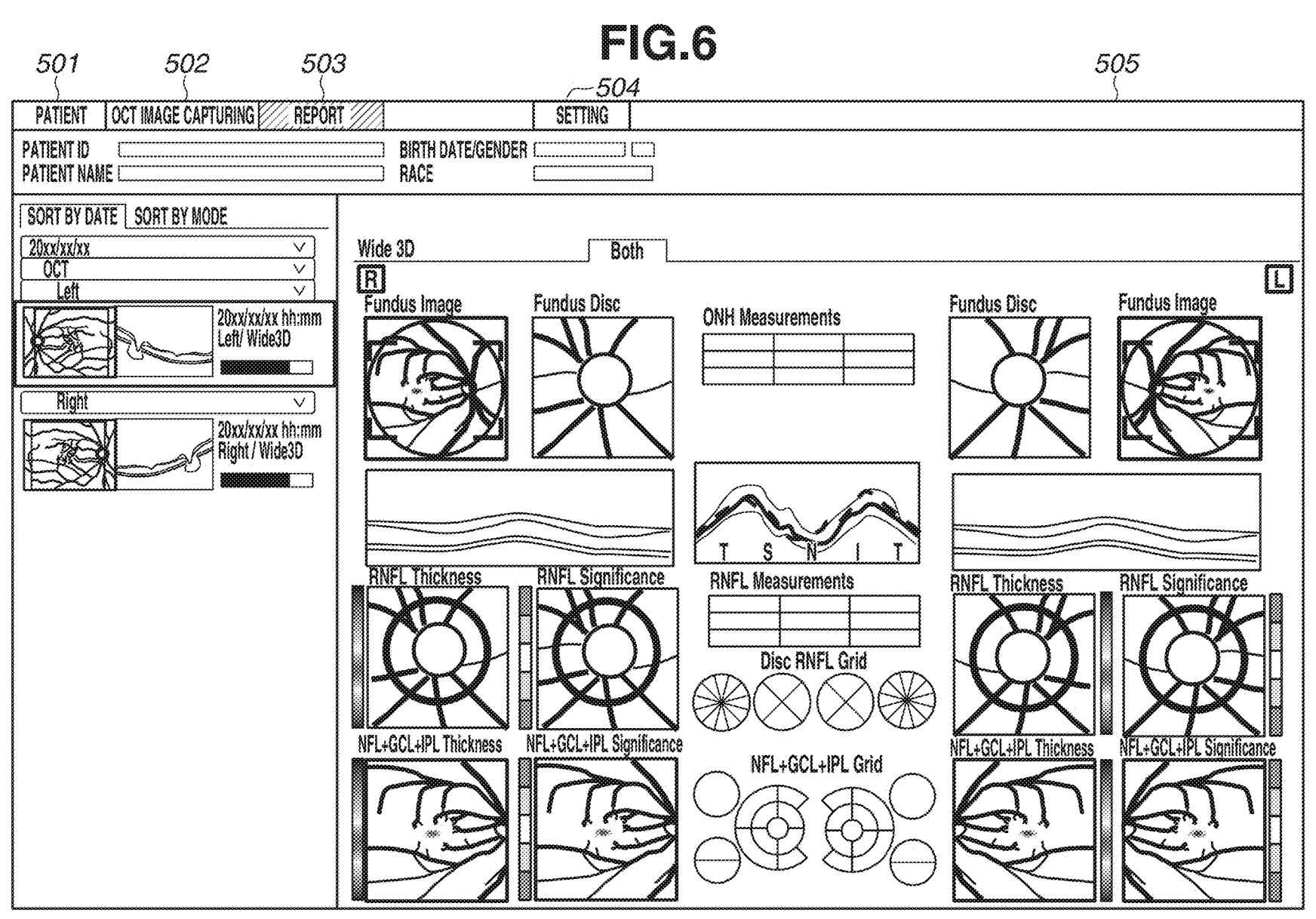

FIGS. 5A and 5B illustrate a display example in the case of displaying one eye. FIG. 6 illustrates an example of simultaneously displaying both eyes. In FIG. 6, images and analysis maps described with reference to FIGS. 5A and 5B are displayed in a comparable state. FIG. 6 illustrates an example of simultaneously displaying both eyes, but the display example is not limited to this. For example, an example of displaying images of the same eye with different image capturing times and analysis maps in a comparable state may be used.

On a display screen, an image to be displayed on a report screen can be output by an output unit (not illustrated) in a printable format as a report.

In step S310, an instruction obtaining unit (not illustrated) obtains an instruction indicating whether to end the image capturing of a tomographic image that is performed by the image processing system 100, from the outside. The instruction is input by the operator using the input unit 700. In a case where an instruction to end the processing is obtained (YES in step S310), the image processing system 100 ends the processing. On the other hand, in a case where image capturing is to be continued without ending the processing (NO in step S310), the processing returns to step S302, and image capturing is continued. The processing of the image processing system 100 is performed in the above-described manner.

According to the above-described configuration, a report for glaucoma diagnosis in a layout centered on an optic disk, and a report for macular disease diagnosis in a layout centered on a macular area can be displayed. Thus, processing suitable for a region can be desirably performed on a tomographic image obtained in a wide area, and an analysis result can be effectively presented.

In the first exemplary embodiment, the description has been given of a display configuration in which wide-area image capturing is performed, and analysis results of an optic disk and a macular area can be easily recognized. In a second exemplary embodiment, an example of displaying time-series image data obtained by performing wide-area image capturing will be described. In glaucoma diagnosis, for follow-up of an analysis map for an optic disk and an analysis map for a macular area, past data and current data obtained from the same subject's eye are desired to be compared in some cases. At this time, in some cases, depending on the status of past data, there is no choice but to compare analysis maps obtained by analyzing three-dimensional data obtained by individually capturing images of a region including an optic disk and a region including a macular area in the past, and each analysis map obtained by analyzing three-dimensional data obtained by capturing an image of a region including an optic disk and a macular area at the present day, for example. As one object, the present exemplary embodiment aims to enhance convenience for an examiner performing a diagnosis. The description of the components having functions similar to those in the above-described first exemplary embodiment will be omitted.

Figure 7:
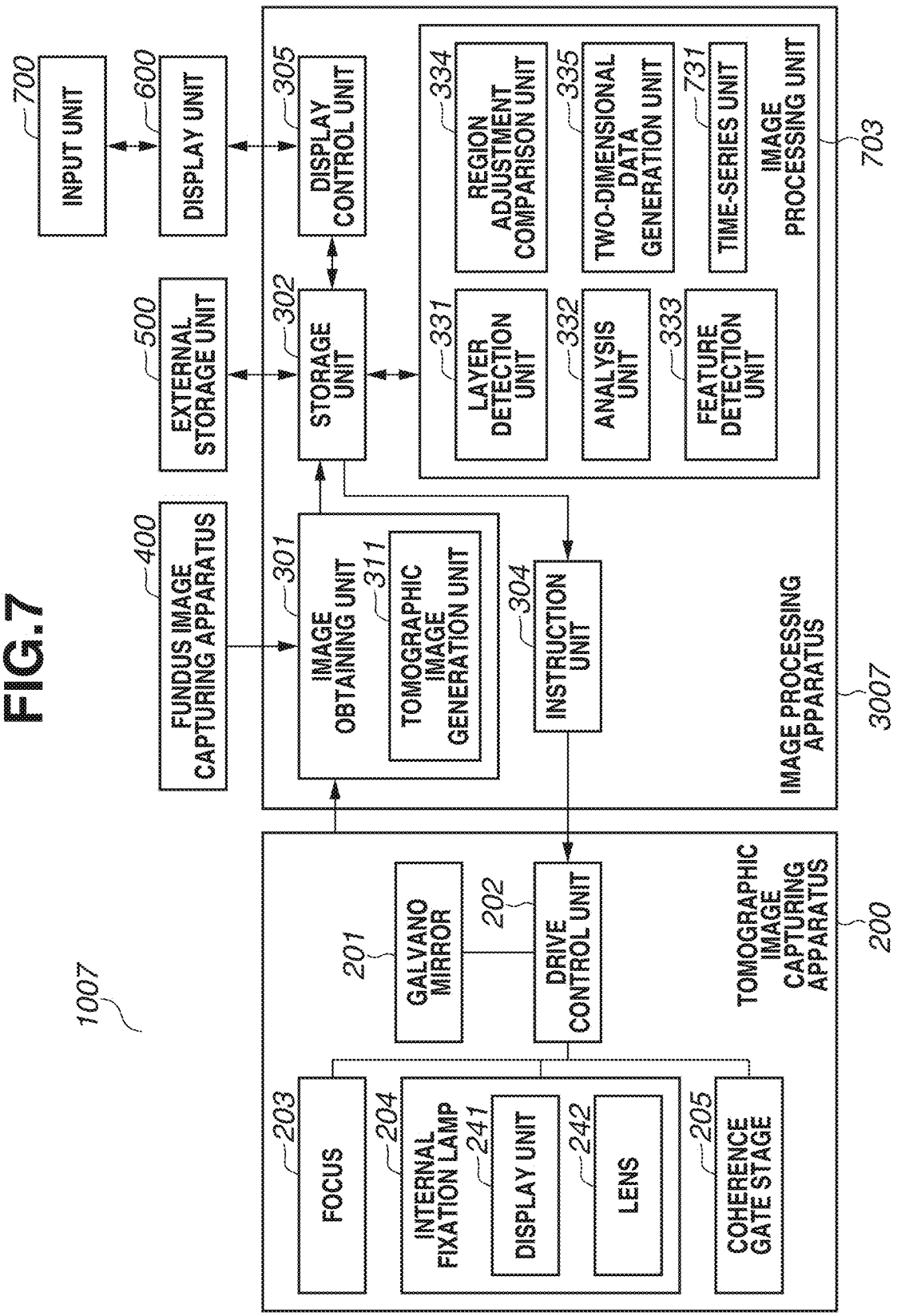
FIG. 7 is a block diagram illustrating a configuration of an image processing system.

FIG. 7 is a block diagram illustrating a configuration of an image processing system 1007 including an image processing apparatus 3007 according to the present exemplary embodiment. As illustrated in FIG. 7, the image processing apparatus 3007 includes an image processing unit 703, and the image processing unit 703 includes a time-series unit 731. The time-series unit 731 performs data selection for making a comparison as follow-up.

Figure 8A:
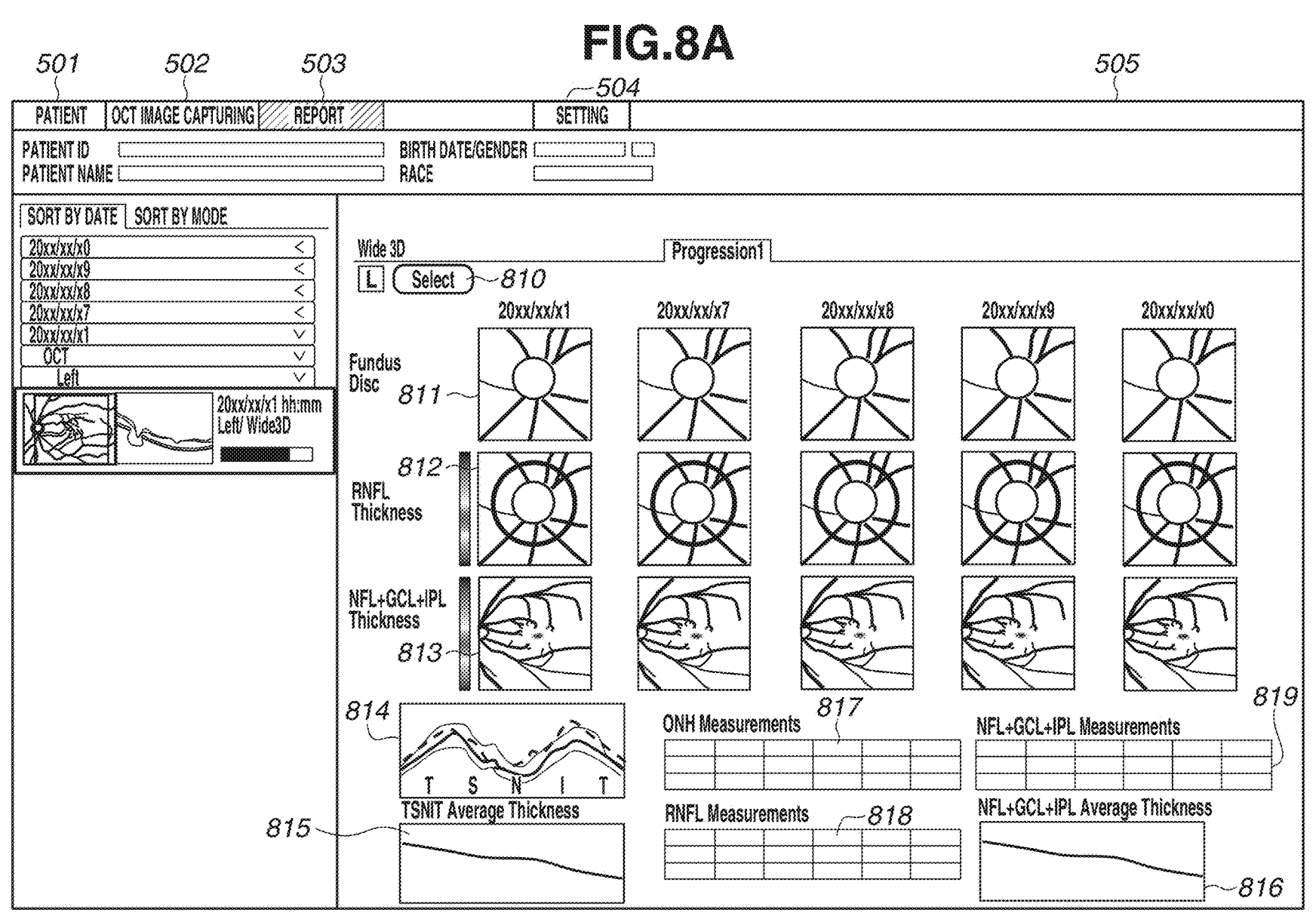
Figure 8B:
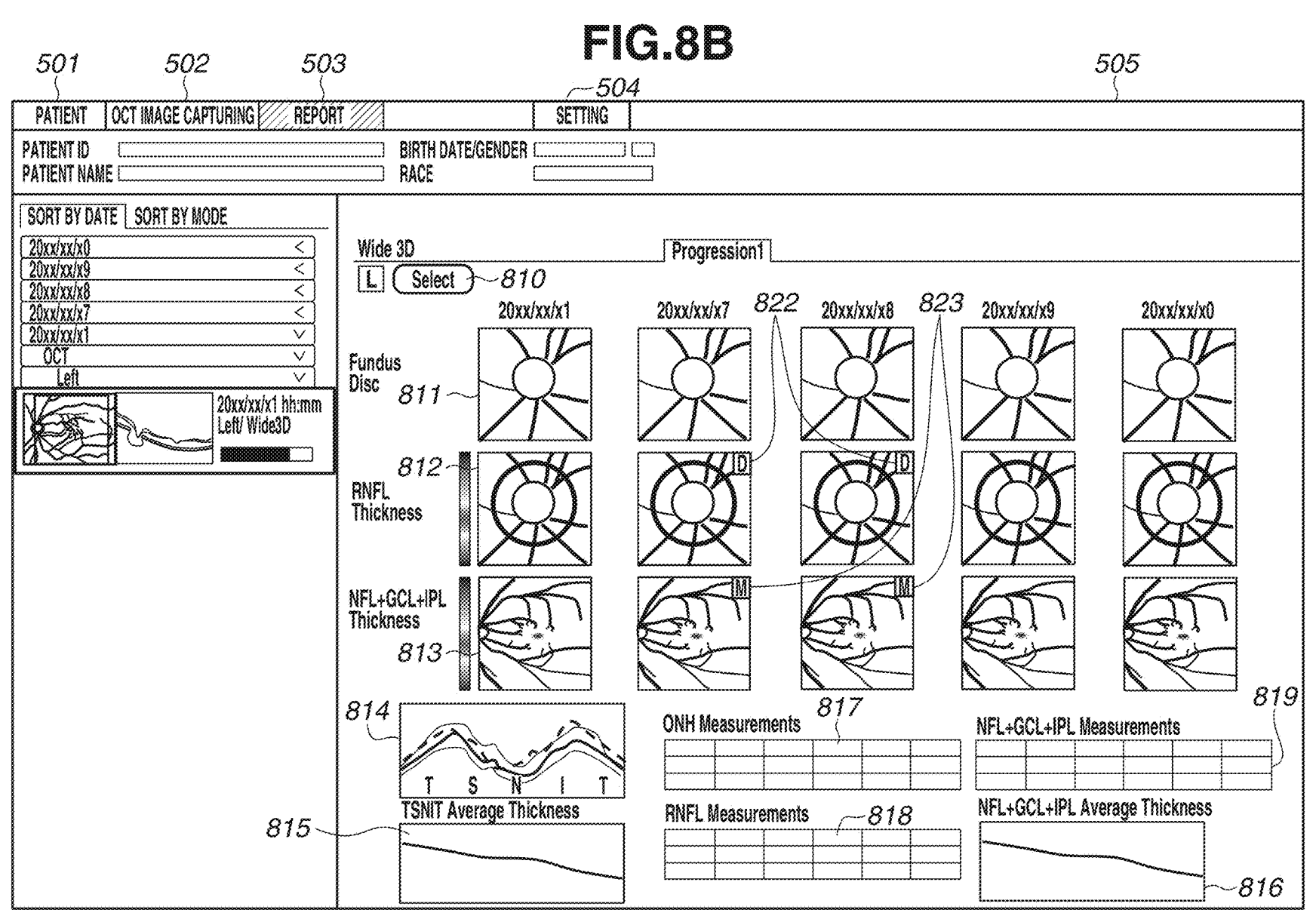
Figure 10A:
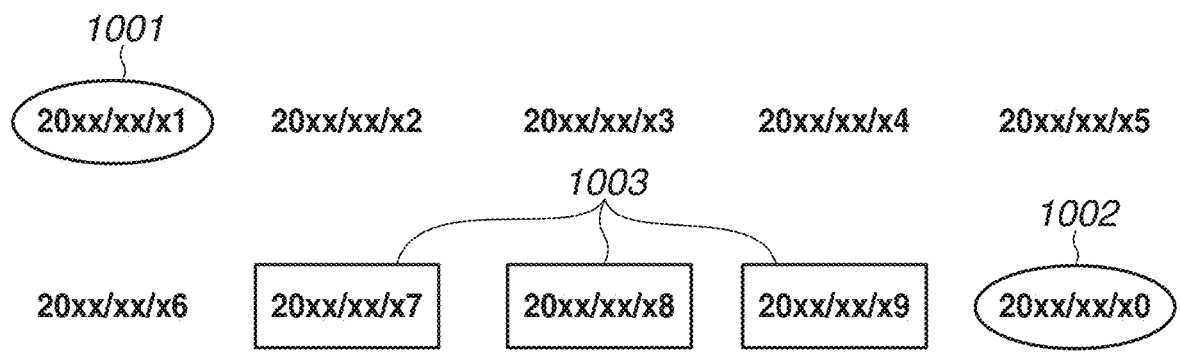
FIGS. 10A and 10B are diagrams illustrating time-series data selection.
Figure 10B:
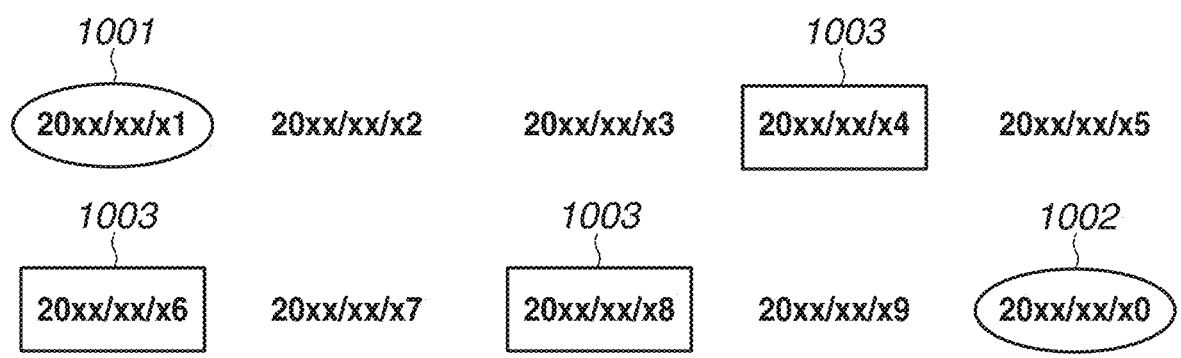

In the present exemplary embodiment, the description will be given assuming that image capturing as described in the above-described first exemplary embodiment has been performed a plurality of times on different days, and a plurality of pieces of data have been already obtained. In this regard, FIGS. 8A and 8B each illustrate an example of displaying side by side a plurality of pieces of time-series data as follow-up. FIG. 8A illustrates an example of chronologically (in time series) arranging data obtained by the region adjustment comparison unit 334 extracting regions of an optic disk and a macular area from data obtained by performing wide-area image capturing. FIG. 8B illustrates an example of chronologically arranging data obtained by performing wide-area image capturing and data obtained by capturing detailed images of an optic disk and a macular area. FIG. 9 is a flowchart illustrating a flow of data selection of time-series data that is performed by the time-series unit 731 according to the present exemplary embodiment. FIGS. 10A and 10B are diagrams illustrating data selection from a plurality of selected data candidate days.

The selection and display of time-series data will be described with reference to FIGS. 8A and 8B to 10A and 10B.

In steps S901 to S903, a condition of data to be selected in addition to reference data is obtained. As a data condition, for example, a flag indicating 0 or 1 is obtained. In a case where there is a plurality of conditions, a value indicated by the flag needs not be limited to 0 or 1.

In step S901, when image capturing is performed a plurality of times using the same scan pattern on the same day, whether to make data of the same day selectable is obtained. In a case where data of the same day is not selectable (NO in step S901), a flag indicating 1 is obtained. In a case where data of the same day is selectable (YES in step S901), a flag indicating 0 is obtained. In a case where data of the same day is not selectable, if a plurality of pieces of data exists on the same day, NG is not set as image capturing data, and the latest data on the same day is selected. In the present exemplary embodiment, the description will be given assuming that a flag indicating 1 is obtained.

In step S902, when images of an optic disk and a macular area are captured in addition to wide-area image capturing, whether to include optic disk data and macular area data as a comparison target is obtained. In a case where only data obtained by wide-area image capturing is to be included as a comparison target (YES in step S902), a flag indicating 1 is obtained. In a case where data obtained by capturing images of an optic disk and a macular area are to be included (NO in step S902), a flag indicating 0 is obtained. In the present exemplary embodiment, FIG. 8A illustrates a display example in a case where a flag indicating 1 is obtained in step S902, and FIG. 8B illustrates a display example in a case where a flag indicating 0 is obtained in step S902. The description of FIGS. 8A and 8B will be given below.

In step S903, a flag regarding data to be selected in addition to the reference data is obtained. For example, as a selection method, a plurality of pieces of data of the latest date is selected, or data between reference data and data of the latest date is selected at equal interval. In the present exemplary embodiment, a flag indicating 1 is obtained. An example of data selection will be described with reference to the next step S905 and FIGS. 10A and 10B.

In step S904, the time-series unit 731 performs selection of reference data. The reference data is data to be referred to when a change in analysis value is measured. Data obtained by performing wide-area image capturing for the first time is selected as the reference data from among pieces of data of a targeted subject's eye. Alternatively, an operator can select arbitrary reference data using a reference data setting unit (not illustrated). In a case where a flag indicating 0 is obtained in step S902, data obtained by capturing an image of a subject's eye for the first time is selected as reference data from among data obtained by performing wide-area image capturing, and data obtained by capturing images of an optic disk and a macular area.

In step S905, data other than reference data and latest data is selected.

The data selection will be described with reference to FIGS. 10A and 10B. The description will be given of a case where selected data candidate days are ten days, and selected data corresponding to three days have been obtained. Data obtained by performing image capturing using a desired scan pattern on each date exists. FIG. 10A illustrates an example of selecting a plurality of pieces of data of the latest date (flag indicates 1 in step S903). FIG. 10B illustrates an example of selecting data between reference data and data of the latest date at equal intervals (flag indicates 0 in step S903). Circled data 1001 indicates an example of reference data, circled data 1002 indicates an example of latest data, and rectangular data pieces 1003 indicate examples of selected pieces of comparison data.

FIGS. 10A and 10B illustrate data corresponding to ten days, as selected data candidate days. In the present exemplary embodiment, in a date list to be displayed as selected data candidate days, dates on which wide-area image capturing data, optic disk image capturing data, and macular area image capturing data have been obtained are displayed. In a case where desired image capturing data does not exist, no candidate is displayed in a list of selected data candidate days as candidates. More specifically, in a case where a flag indicating 1 is obtained in step S902, a date on which wide-area image capturing data has been obtained is displayed in the list of selected data candidate days. In a case where a flag indicating 0 is obtained in step S902, a date on which wide-area image capturing data, or data obtained by capturing an image of an optic disk or a macular area has been obtained is displayed in the list of selected data candidate days.

FIGS. 10A and 10B illustrate an example case where the number of image capturing data is larger than the number of selected data. In a case where the number of image capturing data is smaller than the number of selected data, data to be selected becomes the same irrespective of the setting of the flag in step S903. For example, in a case where selected data candidate days are four days, when reference data and latest data are excluded, the number of comparison data becomes two. In this case, if the number of selected data is three, whichever condition is used, comparison data corresponding to two days are selected.

In step S906, time-series data is displayed. The display of time-series data will be described with reference to FIGS. 8A and 8B.

FIG. 8A illustrates an example of chronologically arranging data obtained by the region adjustment comparison unit 334 extracting regions of an optic disk and a macular area from data obtained by performing wide-area image capturing. In other words, FIG. 8A illustrates a case where a flag indicating 1 is obtained in step S901, a flag indicating 1 is obtained in step S902, and a flag indicating 1 is obtained in step S903. In FIG. 8A, a button 810 is a button for an operator selecting arbitrary data. In the display of time-series data, an image selected based on the flow in FIG. 9 is automatically displayed. However, the operator can select data different from the automatically selected data, by pressing the button 810. An image 811 is an enlarged image of an optic disk periphery from a fundus image. In a case where a fundus image is not captured, an enlarged image of an optic disk periphery from another image captured as a fundus front image such as an SLO image or an infrared image is displayed.

In addition, a map 812 is a layer thickness map indicating the thickness of the RNFL. In addition, a map 813 is a layer thickness map indicating the thickness of a composite layer of the NFL, the GCL, and the IPL. Hereinafter, the display in which the plurality of layer thickness maps is chronologically arranged will be referred to as display of time-series data. At this time, past layer thickness maps in time-series data of the layer thickness maps 812 and 813 are examples of a first analysis map for an optic disk and a second analysis map for a macular area, which are analysis results of three-dimensional data obtained by capturing an image of a region including an optic disk and a macular area at a first time using the OCT. In addition, current (latest) layer thickness maps in time-series data of the layer thickness maps 812 and 813 are examples of a third analysis map for an optic disk and a fourth analysis map for a macular area, which are analysis results of three-dimensional data obtained by capturing an image of a region including an optic disk and a macular area at a second time later than the first time using the OCT. At this time, the display control unit 305 can control the display unit 600 to display a plurality of analysis maps for the optic disk (first analysis map and third analysis map) in time series arranged manner in a first display region (e.g., region in which the time-series data of the layer thickness map 812 is displayed). In addition, the display control unit 305 can control the display unit 600 to display a plurality of analysis maps for the macular area (second analysis map and fourth analysis map) in time series arranged manner in a second display region different from the first display region (e.g., region in which the time-series data of the layer thickness map 813 is displayed).

A thickness profile 814 is a thickness profile of the RNFL at a circle position of the optic disk periphery, and indicates a plurality of thickness profiles corresponding to time-series data. A graph 815 is a chronological change graph of the thickness of TSNIT. A vertical axis of the graph indicates a thickness, and a horizontal axis of the graph indicates an image capturing day. Tables 817 and 818 list measurement values regarding an optic disk and the thickness of the RNFL. For example, Disc areas, Rim areas, C/D ratios, and average values of thickness of TSNIT of the RNFL are chronologically displayed. A graph 816 is a chronological change graph of the thickness of the composite layer of the NFL, the GCL, and the IPL. A table 819 chronologically displays average values of thicknesses of the composite layer of the NFL, the GCL, and the IPL.

The description has been given of an example in which layer thickness maps indicating the thicknesses are chronologically displayed in the maps 812 and 813. However, maps are not limited to these, and a Significance map and a Deviation map may be displayed. Furthermore, a Difference map indicating a difference from a map serving as a base may be displayed. The switching between these map images is performed in such a manner that, if one map changes, the remaining maps switch in synchronization with the change.

FIG. 8B illustrates an example of chronologically arranging data obtained by performing wide-area image capturing and data obtained by capturing detailed images of an optic disk and a macular area. In other words, FIG. 8B illustrates a case where a flag indicating 1 is obtained in step S901, a flag indicating 0 is obtained in step S902, and a flag indicating 1 is obtained in step S903. In FIG. 8B, maps 822 and 823 indicate examples of data obtained by capturing detailed images of an optic disk and a macular area, and pieces of remaining data are examples of data obtained by performing wide-area image capturing (an example of an analysis result of three-dimensional data obtained by performing image capturing in an image capturing mode for capturing an image of a region including an optic disk and a macular area). In the map 822, an icon indicating that the data is data obtained by capturing an image of an optic disk (an example of an analysis result of three-dimensional data obtained by performing image capturing in an image capturing mode for individually capturing an image of an optic disk) is displayed. In addition, in the map 823, an icon indicating that the data is data obtained by capturing an image of a macular area (an example of an analysis result of three-dimensional data obtained by performing image capturing in an image capturing mode for individually capturing an image of a macular area) is displayed. Such display needs not be performed using an icon. It is sufficient that an index for making an operator recognize that data is different from data obtained by performing wide-angle image capturing is displayed by providing, for example, color display in the periphery of an image, or changing the color of a date displayed in an upper part of an image. In other words, the display control unit 305 may display, on the display unit 600, information indicating that the first and second analysis maps to be described below, and the third and fourth analysis maps are distinguishable from each other, and are analysis results of three-dimensional data obtained by performing image capturing in different image capturing modes. As the data obtained by capturing detailed images of an optic disk and a macular area is selected, graphs and measurement values to be displayed in the thickness profile 814 to the table 819 display numerical values calculated from the data.

In other words, among time-series data, data obtained by capturing a detailed image of an optic disk is the first analysis map that is an analysis result of three-dimensional data of an optic disk obtained by capturing an image of a region including an optic disk at the first time using the OCT, for example. In addition, among time-series data, data obtained by capturing a detailed image of a macular area is the second analysis map that is an analysis result of three-dimensional data of a macular area obtained by capturing an image of a region including a macular area at the first time using the OCT, for example. The first time at which the image of the region including the optic disk is captured, and the first time at which the image of the region including the macular area is captured need not be exactly the same, and are only required to be on the same date, for example. In addition, among time-series data, pieces of data obtained by performing wide-area image capturing are the third analysis map for an optic disk and the fourth analysis map for a macular area that are analysis results of three-dimensional data obtained by capturing an image of a region including an optic disk and a macular area at the second time later than the first time using the OCT, for example. At this time, the display control unit 305 can control the display unit 600 to display the first analysis map and the third analysis map in time series arranged manner in the first display region (e.g., region in which time-series data of the layer thickness map 812 is displayed). In addition, the display control unit 305 can control the display unit 600 to chronologically display the second analysis map and the fourth analysis map in time series arranged manner in the second display region different from the first display region (e.g., region in which the time-series data of the layer thickness map 813 is displayed).

Figure 11:
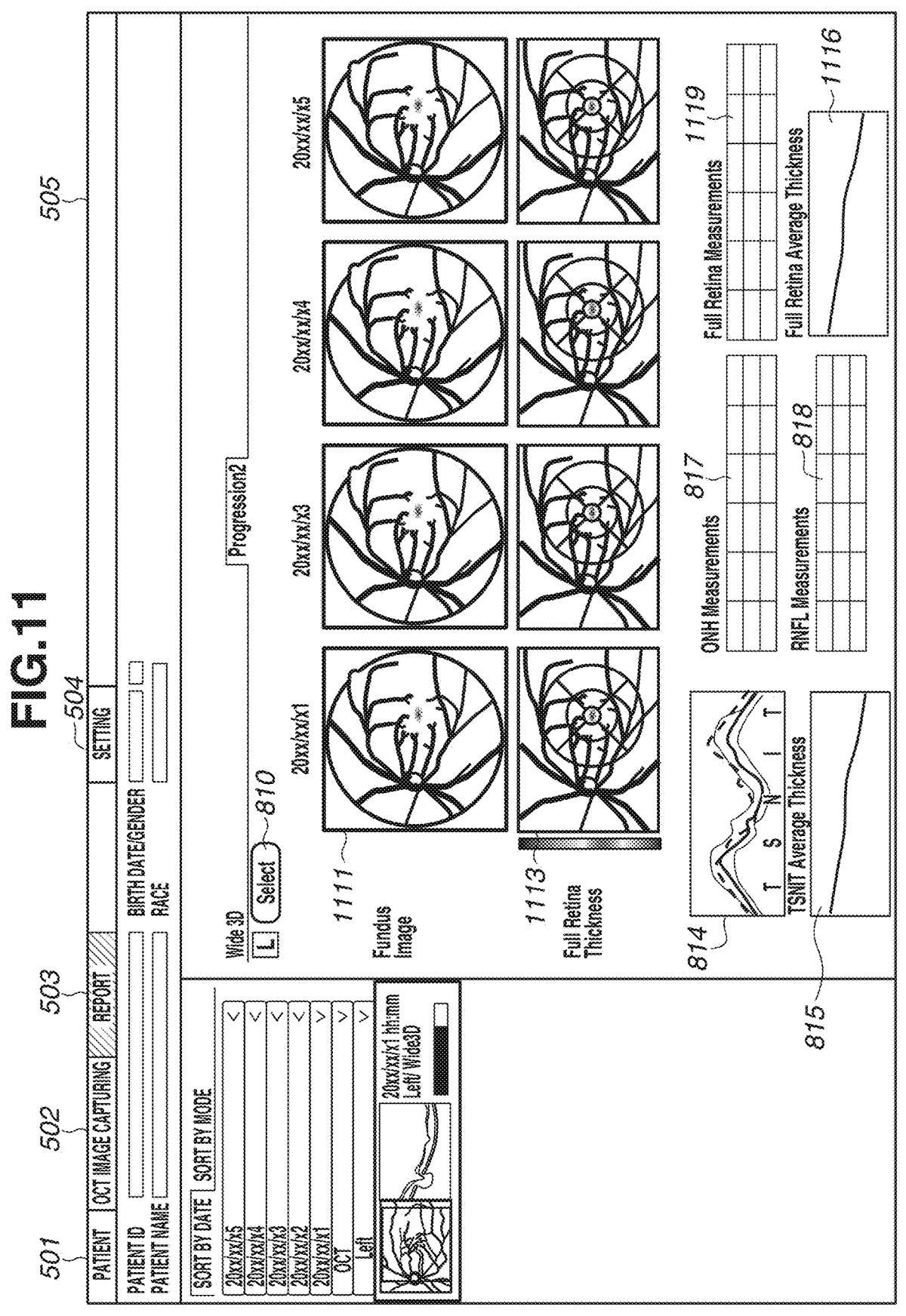

FIG. 8A illustrates an example of arranging data obtained by extracting regions of an optic disk and a macular area from data obtained by performing wide-area image capturing. An example of chronologically displaying data obtained by performing wide-area image capturing is not limited to this. For example, data may be displayed as illustrated in FIG. 11. FIG. 11 illustrates an example of displaying the entire wide-area image without displaying data by extracting regions of an optic disk and a macular area from data obtained by performing wide-area image capturing. An image 1111 is a fundus image, and a map 1113 is a map indicating a layer thickness of the entire retina. A graph 1116 is a chronological change graph of a layer thickness of the entire retina, and a table 1119 chronologically displays an average value of layer thicknesses of the entire retina. FIG. 11 illustrates a layer thickness map indicating the layer thickness of the entire retina, but a layer thickness map indicating the thickness of the RNFL, a layer thickness map indicating the thickness of the composite layer of the NFL, the GCL, and the IPL, a Significance map, and a Deviation map may be displayed.

According to the above-described configuration, based on data obtained by performing wide-area image capturing, analysis results of an optic disk and a macular area can be displayed as time-series image data. Furthermore, data obtained by performing wide-area image capturing, and data obtained by performing detailed image capturing can be displayed as time-series image data.

In the first and second exemplary embodiments, the description has been given of a display configuration in which wide-area OCT images are captured, and analysis results of an optic disk and a macular area can be easily recognized. In a third exemplary embodiment, processing of an example in which wide-area OCT images are captured, and wide-area OCT angiography (OCTA) images are generated and displayed will be described with reference to FIGS. 12 and 13. In the resent exemplary embodiment, a configuration of an image processing system including an image processing apparatus as illustrated in FIGS. 1 and 7 is not illustrated, but the image processing apparatus includes a motion contrast data generation unit.

Figure 12:
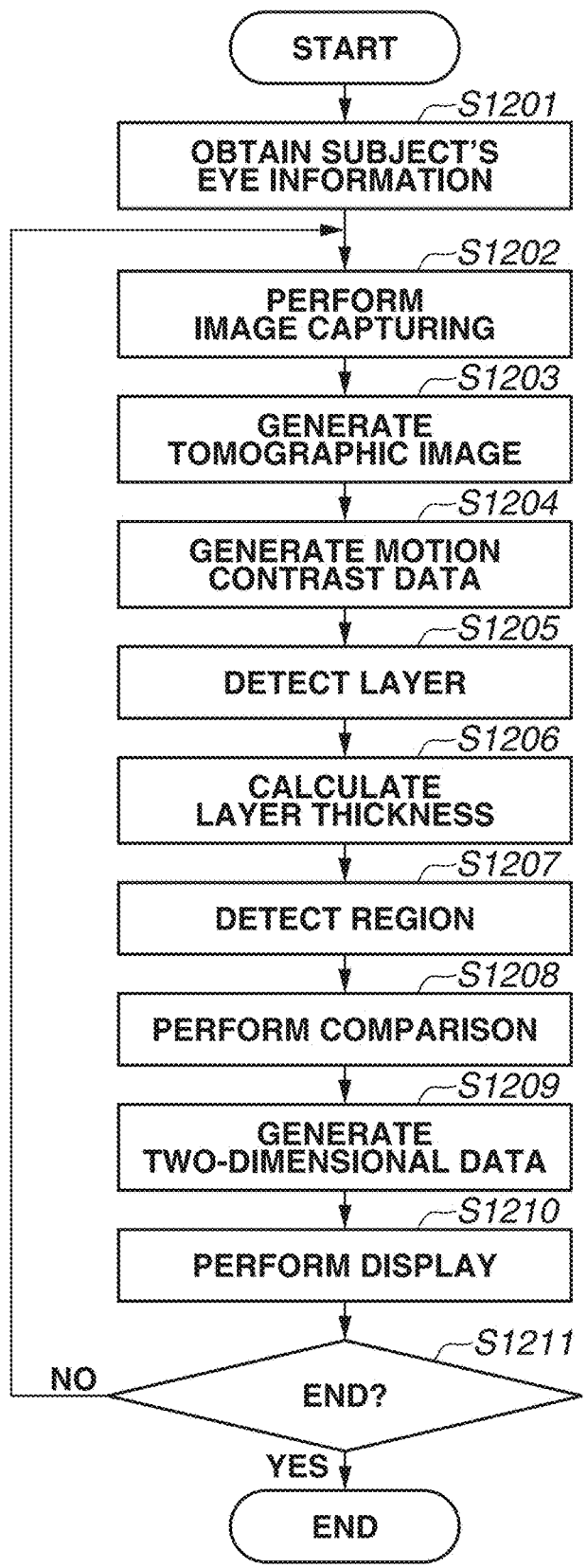
FIG. 12 is a flowchart illustrating a flow of processing in an image processing system.
Figure 13:
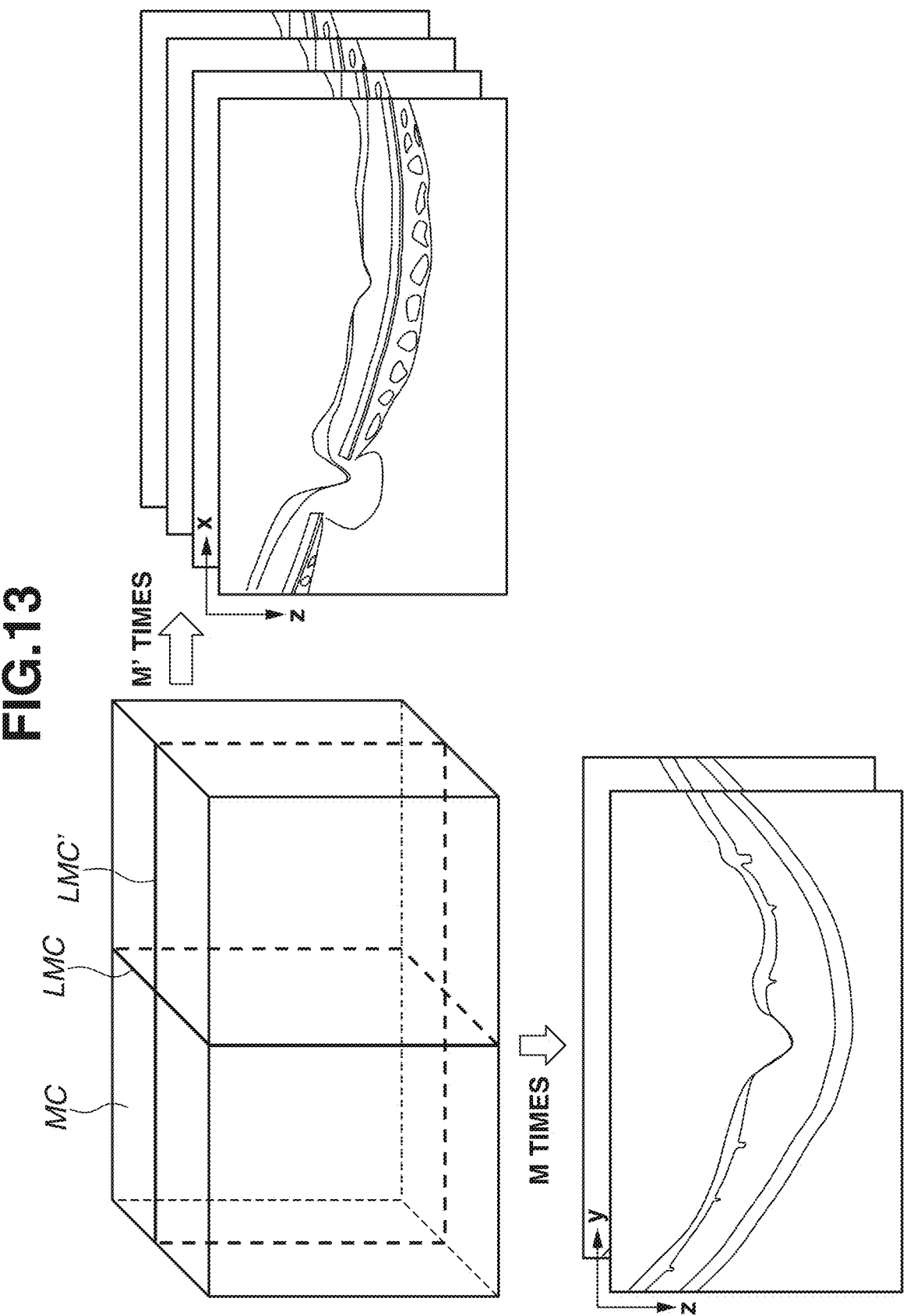
FIG. 13 is a diagram illustrating motion contrast data.

FIG. 12 is a flowchart illustrating processing according to the present exemplary embodiment, and FIG. 13 illustrates operation processing of the entire system according to the present exemplary embodiment. The description of steps having functions similar to those in the above-described first and second exemplary embodiments will be omitted.

In step S1202, image capturing is performed by scanning a subject's eye. In the scan of the subject's eye, if an operator selects a scan start (not illustrated), the tomographic image capturing apparatus 200 controls the drive control unit 202 to operate the galvano mirror 201, and a tomographic image is scanned.

In the present exemplary embodiment, the description will be given assuming that image capturing is performed using a scan pattern for three-dimensional volume that is based on raster scan, and a range of 13×10 mm at an interval of 500×250 (main scanning×sub-scanning), for example. In the three-dimensional volume, for calculating motion contrast, image capturing of the same line point is repeatedly performed M times (M is 2 or more). More specifically, in a case where M is two, actually, data of 500×500 is captured, and three-dimensional motion contrast data of 500×250 is generated from the data. Also in the present exemplary embodiment, as described in the first exemplary embodiment, three-dimensional data generation and horizontal scanning image capturing are performed. By the horizontal scanning, one or a plurality of images (e.g., about ten images) are captured. In the present exemplary embodiment, the description will be given assuming that a plurality of images are captured by the horizontal scanning.

Because the tomographic image capturing apparatus 200 performs image capturing of the same location for addition averaging, by tracking a subject's eye, the tomographic image capturing apparatus 200 can also scan the subject's eye with suppressed influence of an involuntary eye movement. Furthermore, in a case where a motion causing an artifact in generating an image such as blinking is detected, rescan is automatically performed at a location where the artifact occurs.

In step S1204, the motion contrast data generation unit generates motion contrast data. The data generation will be described with reference to FIG. 13. FIG. 13 illustrates three-dimensional motion contrast data MC, and two-dimensional motion contrast data LMC included in the three-dimensional motion contrast data MC. Furthermore, FIG. 13 illustrates horizontal scanning LMC' for capturing an image of the center of a three-dimensional region. In the present exemplary embodiment, an example of the generation of the horizontal scanning LMC' will be described.

The motion contrast data generation unit initially corrects a positional shift among a plurality of tomographic images captured within the same range of the subject's eye. An arbitrary method may be used as a correction method of a positional shift. For example, the motion contrast data generation unit performs image capturing of the same range M' times, and performs position alignment of tomographic image data corresponding to the same point, using features such as a fundus shape. The same point in the present exemplary embodiment is not limited to perfectly matching points, and refers to points including a shift of about several μm to several tens μm generated even if a positional shift of an eye caused by tracking is corrected.

More specifically, one of M' pieces of tomographic image data is selected as a template, a similarity with another tomographic image data is obtained while varying a position and an angle of the template, and a positional shift amount from the template is obtained. Then, the motion contrast data generation unit corrects each piece of tomographic image data based on the obtained positional shift amount.

Next, the motion contrast data generation unit obtains a decorrelation value M (x, z) of two pieces of tomographic image data having consecutive image capturing times, using Formula (1).

$$M(x, z) = 1 - 2 \times \frac{A(x, z) \times B(x, z)}{A(x, z)^2 + B(x, z)^2} \quad (1)$$

In the formula (1), A (x, z) denotes a brightness at a position (x, z) of tomographic image data A, and B (x, z) denotes a brightness at the same position (x, z) of tomographic image data B.

The decorrelation value M (x, z) becomes a value from 0 to 1, and the value of the decorrelation value M (x, z) becomes larger as a difference between the two brightness values becomes larger. In a case where the value M' repeatedly obtained at the same position is 3 or more, the motion contrast data generation unit can obtain a plurality of decorrelation values M (x, z) at the same position (x, z). The motion contrast data generation unit can generate final motion contrast data by performing statistical processing such as maximum value calculation or average calculation of the plurality of obtained decorrelation values M (x, z). In a case where the number of repetitions M is two, statistical processing such as maximum value calculation or average calculation is not performed, and a decorrelation value M (x, z) between two adjacent tomographic images A and B becomes a value of motion contrast at the position (x, z).

The motion contrast calculation expression represented by Formula (1) tends to be susceptible to noise. For example, in a case where noises are included in a non-signal portion of a plurality of tomographic image data, and values are different from each other, decorrelation value becomes higher, and noises are superimposed also on a motion contrast image. To avoid this situation, the motion contrast data generation unit can regard tomographic data with a value falling below a predetermined threshold value, as noises, and replace the value with zero, as preprocessing. An image generation unit can thereby generate a motion contrast image with reduced influence of noise based on the generated motion contrast data.

Furthermore, the motion contrast data generation unit generates a two-dimensional motion contrast front image (also referred to as an OCTA image) from three-dimensional motion contrast data. The motion contrast data generation unit generates an OCTA image by projecting motion contrast data corresponding to a range defined by a generation range upper end and a generation range lower end designated for the three-dimensional motion contrast data, onto a two-dimensional plane. More specifically, based on motion contrast data corresponding to the range between the generation range upper end and the generation range lower end in the entire motion contrast data, the motion contrast data generation unit generates an OCTA image that is a front image of a motion contrast image by performing processing such as average intensity projection (AIP) or maximum intensity projection (MIP) on motion contrast data within the range. The generation method of an OCTA image is not limited to a method that uses an average value or the maximum value. The OCTA image may be generated using a value such as a minimum value, a median value, a variance, a standard deviation, or a sum.

For example, as an OCTA image that generates retina superficial layer portion (superficial), the generation range upper end is defined as a boundary line between the ILM and the NFL, and the generation range lower end is defined as a boundary line at the 50-μm lower end in the depth direction from the GCL/IPL. Then, an OCTA image is generated by the MIP.

As a generation timing of an OCTA image, several types of images having different depth ranges may be preliminarily generated, or an image corresponding to the generation range upper end and the generation range lower end designated via a user interface may be generated at a display timing on a display unit.

Because steps S1205 to S1208 are similar to the steps S304 to S307 described according to the first exemplary embodiment, the description will be omitted.

In step S1209, an analysis map described in step S308 is generated, and moreover, the two-dimensional data generation unit 335 generates an analysis map from the OCTA image. The analysis map is subjected to blood vessel enhancement processing that is based on a hessian filter and edge selective sharpening. Then, binarization processing is performed using two types of blood vessel enhanced images, and a blood vessel region is identified by performing shaping processing. An example of blood vessel detection that uses image processing has been described, but blood vessel detection is not limited to this. By learning images and correct labels using a machine learning method such as deep learning, a blood vessel may be detected from an input image.

In the case of analyzing an OCTA image, maps of a Vessel Area Density (VAD) that is based on an area of the blood vessel region, and a Vessel Length Density (VLD) that is based on a blood vessel length are generated. The VAD is a vascular density (unit: %) defined by a percentage of the blood vessel region included in a measurement target. In addition, the VLD is a vascular density defined by a sum (unit: mm−1) of lengths of blood vessels included per unit area.

The vascular density is an index for quantifying the extent of vessel occlusion or the extent of sparseness/denseness of vascular networks, and the VAD is used most frequently. However, because a large vessel region has a large extent of contribution in measurement values of VAD, in a case where measurement is to be performed while paying attention to capillary disease states such as retinopathy of diabetes, the VLD is used as an index more sensitive to capillary occlusion.

The measurement is not limited to this. For example, a Fractal Dimension for quantifying the complexity of a blood vessel structure, or a Vessel Diameter Index indicating a distribution of blood vessel diameters (distribution of bump or narrowing of blood vessels) may be measured.

Figure 14:
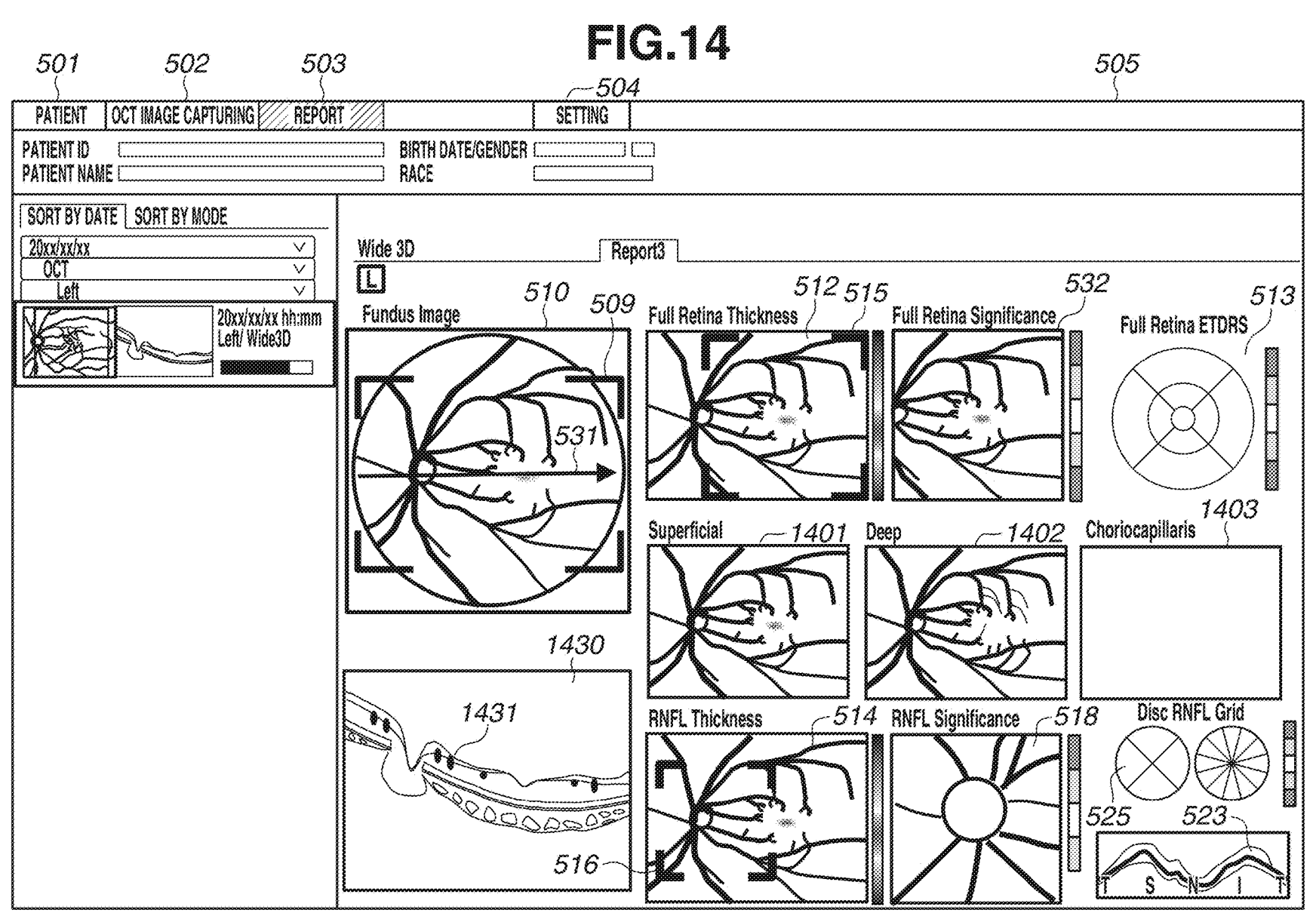

In step S1210, a captured image, a layer thickness map, and an analysis map are displayed on the display unit 600. FIG. 14 illustrates an example of a screen to be displayed on the display unit 600.

FIG. 14 illustrates an example of displaying a motion contrast tomographic image and a motion contrast front image (OCTA image) based on the display example illustrated in FIG. 5B.

An image 1401 displays an OCTA image of a retina superficial layer portion (Superficial), an image 1402 displays an OCTA image of a retina deep layer portion (Deep), and an image 1403 displays an OCTA image of choriocapillaris. FIG. 14 illustrates the display of OCTA images, but images are not limited to OCTA images. Using a user interface (not illustrated) (e.g., button, right click menu, tab switching, checkbox, long tap, multitap, etc.), a map indicating a vascular density (VAD or VLD) by pseudo color can be displayed in a superimposed manner on an OCTA image by setting permeability.

A tomographic image 1430 is a tomographic image of horizontal scanning, and a region 1431 related to motion contrast data is displayed in a superimposed manner on the tomographic image 1430. The region 1431 indicates, for example, data having a value equal to or larger than a threshold value in motion contrast data generated from a plurality of horizontal scanning tomographic images. In the superimposed display of motion contrast data, display and non-display can be switched. Furthermore, execution of projection artifact prevention processing can also be designated. A three-dimensionally-captured tomographic image of vertical scan may be displayed in place of the tomographic image 1430 of the horizontal scanning, or the tomographic image of vertical scan may be displayed side by side to the tomographic image of the horizontal scanning, which is not illustrated in FIG. 14. motion contrast data is displayed in a superimposed manner also in the tomographic image of the vertical scan.

As compared with the display example illustrated in FIG. 5B, the thickness of a composite layer of the NFL, the GCL, and the IPL, a Significance map, and a Deviation map are not displayed, but these maps can be displayed in place of the map 512 indicating the thickness of the entire retina, and a Significance map for the thickness of the entire retina, by switching the display. In a case where the thickness is switched between the thickness of the entire retina and the thickness of the composite layer of the NFL, the GCL, and the IPL, a grid displaying measurement values is also displayed by being switched from the grid 513 to the grid 526 in response to the switching of the thickness.

As exemplified in FIGS. 8A and 8B and 11, other than layer thickness maps, Significance maps, and Deviation maps, OCTA images and vascular density map images can also be chronologically displayed, which are not illustrated. For example, the description will be given with reference to FIG. 11. In place of the layer thickness map 1113 indicating the thickness of the retina entire layer, an OCTA image 1401 may be displayed, and a vascular density map may be displayed in a superimposed manner on the OCTA image.

According to the above-described configuration, wide-area OCT images can be captured, and wide-area OCT angiography images can be generated and displayed, processing suitable for a region can be performed, and an analysis result can be effectively presented.

In the first to third exemplary embodiments, the description has been given of a display configuration in which wide-area OCT images are captured, and analysis results of an optic disk and a macular area, and an analysis result of an OCTA image can be easily recognized. In a fourth exemplary embodiment, an example of performing image quality improvement processing on at least one of a wide-area OCT image, an OCTA image, and a fundus image using an image quality improvement unit will be described. The image quality improvement processing refers to noise removal, super-resolution, and contrast adjustment processing.

Figure 15:
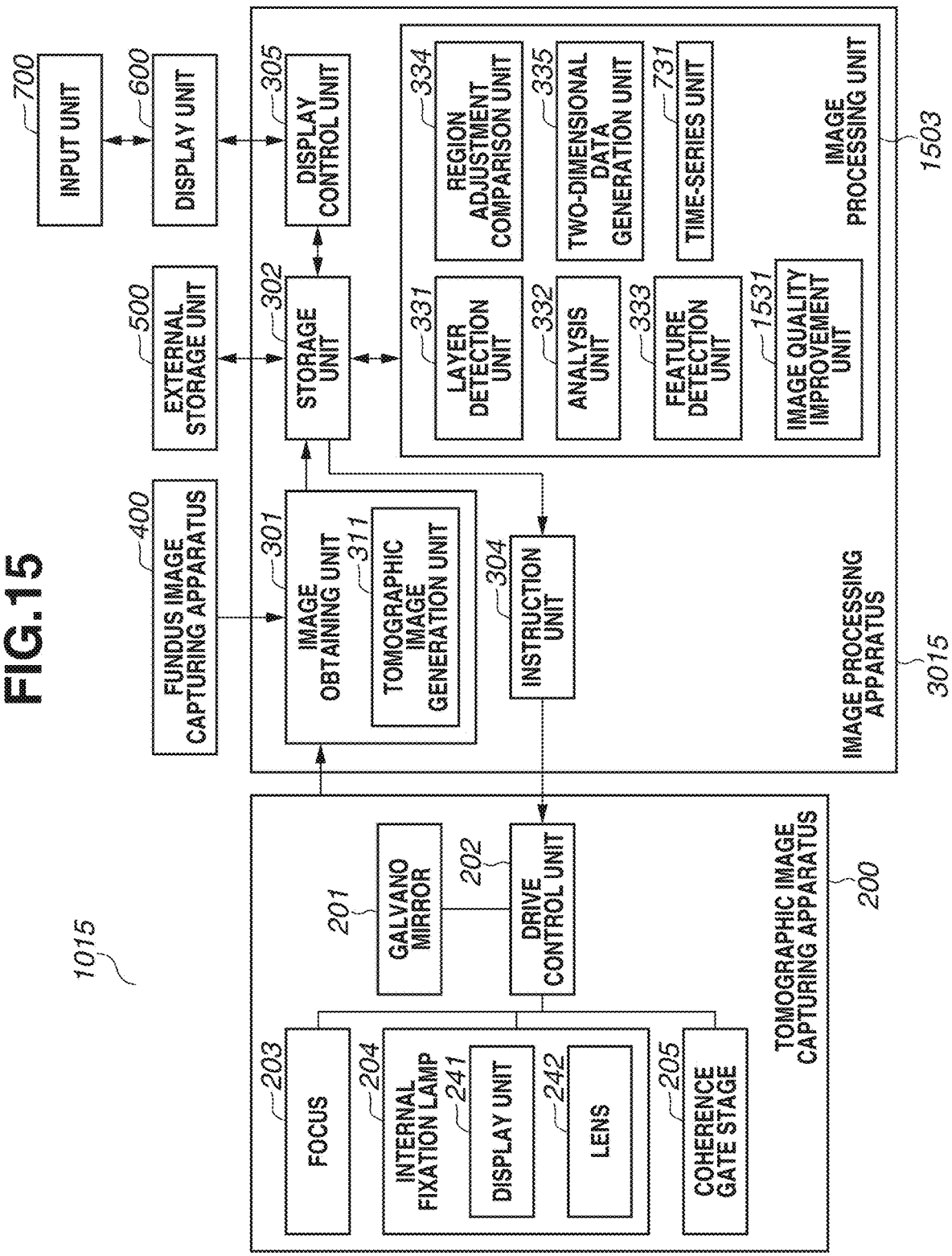
FIG. 15 is a block diagram illustrating a configuration of an image processing system.

FIG. 15 is a block diagram illustrating a configuration of an image processing system 1015 including an image processing apparatus 3015 according to the present exemplary embodiment. As illustrated in FIG. 15, the image processing apparatus 3015 includes an image processing unit 1503, and the image processing unit 1503 includes an image quality improvement unit 1531. The image quality improvement unit 1531 performs image quality improvement of an image using a machine learning model.

Figure 16:
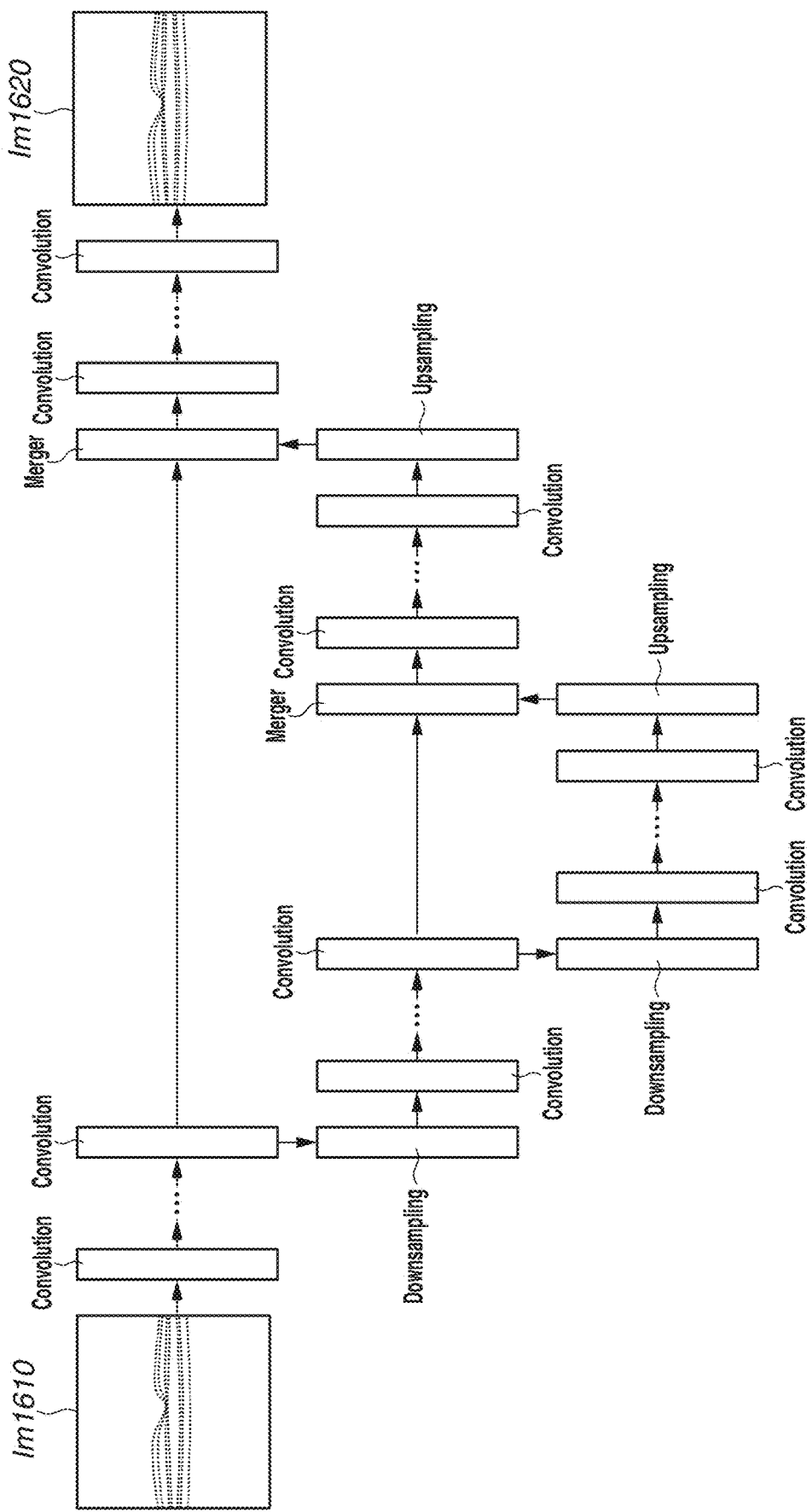
FIG. 16 is a diagram illustrating a machine learning model.

In the present exemplary embodiment, image quality improvement using noise removal will be described. FIG. 16 illustrates an example of a configuration of a machine learning model according to the present exemplary embodiment. The configuration illustrated in FIG. 16 includes a plurality of layer groups having a function of processing an input value group and outputting the processed input value group. As illustrated in FIG. 16, the types of layers included in the above-described configuration include a convolution layer, a downsampling layer, an upsampling layer, and a merger layer. The convolution layer is a layer that performs convolution processing on an input value group based on parameters such as a kernel size of a set filter, the number of filters, a value of stride, and a value of dilatation. A dimension number of a kernel size of the filter may be changed depending on a dimension number of an input image. The downsampling layer performs processing of making the number of output value groups smaller than the number of input value groups by thinning out or merging input value groups. More specifically, for example, the processing includes Max Pooling processing. The upsampling layer performs processing of making the number of output value groups larger than the number of input value groups by copying an input value group, or adding a value interpolated from an input value group. More specifically, for example, the processing includes linear interpolation processing. The merger layer is a layer that performs processing of inputting value groups such as an output value group of a certain layer or a pixel value group constituting an image, from a plurality of sources, and merging the value groups by connecting or adding these value groups. In such a configuration, a pixel value group constituting an input image Im1610 that has been output after passing through a convolution processing block, and a pixel value group constituting the input image Im1610 are merged by the merger layer. Then, the merged pixel value group is formed into a high quality image Im1620 by a last convolution layer. FIG. 16 illustrates tomographic images as images Im1610 and Im1620, but a retina front image such as a motion contrast tomographic image, a motion contrast front image (OCTA image), an Enface image, an SLO image, or a fundus image can also be used. An imaging range is not limited to a posterior eye portion of retina, and may be an anterior eye portion.

As a change example of a configuration of a CNN, for example, a batch normalization layer or an activation layer that uses a rectifier linear unit may be added after the convolution layer, which is not illustrated in FIG. 16.

An image quality improvement engine according to the present exemplary embodiment performs training by inputting a low quality image obtained by adding a first noise component to an image obtained from the tomographic image capturing apparatus 200 or another apparatus, and outputting, as output data, a high quality image obtained by adding a second noise component to the image obtained from the tomographic image capturing apparatus 200 or another apparatus. In other words, as supervised images in learning according to the present exemplary embodiment, the low quality image and the high quality image are obtained by using a common image, and noise components in these images are different. Because the same original image is used, position alignment for making pair images is unnecessary.

A learning unit may include an error detection unit (not illustrated) and an update unit (not illustrated). The error detection unit obtains an error between supervised data and output data output from an output layer of a neural network corresponding to input data input to an input layer. The error detection unit may calculate an error between the supervised data and the output data from a neural network using a loss function. In addition, based on the error obtained by the error detection unit, the update unit updates an internode connection weighting coefficient of a neural network so as to reduce the error. The update unit updates a connection weighting coefficient using, for example, backpropagation method. The backpropagation method is a method of adjusting an internode connection weighting coefficient of each neural network so as to reduce the above-described error.

At this time, a graphics processing unit (GPU) can perform efficient calculation by concurrently processing a larger amount of data. Thus, in a case of performing learning a plurality of times using a learning model such as deep learning, it is effective to perform processing using a GPU. Thus, in the present exemplary embodiment, a GPU is used in addition to a central processing unit (CPU) in processing to be performed by the learning unit. More specifically, in a case of executing a learning program including a learning model, learning is performed by the CPU and the GPU performing calculation in cooperation. In the processing of the learning unit, calculation may be performed only by the CPU or the GPU. In addition, the image quality improvement unit 1531 may also use a GPU similarly to the learning unit.

In addition, as noise components, a Gaussian noise or a noise obtained by modeling a noise specific to a target image is added as a noise. A first noise and a second noise are different noises. The different noises mean that noises different in spatial location (pixel position) to which noises are added, or noises different in noise value. As for a noise specific to a target image, for example, in the case of OCT, noises are estimated based on data obtained by performing image capturing in a state in which a model eye or a subject's eye is not placed, and the estimated noises can be used as a noise model. In the case of OCTA, noises can be used as a noise model based on a noise appearing in a foveal avascular zone (FAZ) or a noise appearing in a captured image of a model eye schematically imitating a flow of blood.

In the case of a Gaussian noise, a standard deviation or a variance value is defined as the magnitude of a noise, and noises are added to an image at random based on these numerical values. Random noises may be added in such a manner that an average value as a whole does not change. In other words, noises are added in such a manner that an average value of noises to be added to each pixel of one image becomes 0. There is no need to add noises in such a manner that the average value becomes 0, and it is sufficient that noises with different patterns can be added to input data and output data.

In the present exemplary embodiment, a high quality image is generated using an image obtained by adding a first noise component and a second noise component different from the first noise component to a low quality image obtained from the tomographic image capturing apparatus 200 or another apparatus, but a configuration of performing such processing is not limited to this. For example, the first and second noise components may be added to a high quality image having been subjected to addition average processing (superimposition) after performing position alignment, as an image to which noises are added. In other words, learning may be performed using an image obtained by adding the first noise component to a superimposed image, as a low quality image, and an image obtained by adding the second noise component to a superimposed image, as a high quality image. Furthermore, in the present exemplary embodiment, an example of performing learning using the first and second noise components has been described, but the learning is not limited to this. For example, learning may be performed by adding the first noise component only to an image used as a low quality image, without adding a noise component to an image used as a high quality image.

In a case where super-resolution processing is performed as image quality improvement processing, learning is only required to be performed using a low resolution image and a high resolution image as a pair. In a case where contrast adjustment processing is performed, learning is performed using a low contrast image and a high contrast image as a pair. There is no need to perform uniform adjustment on a high contrast image serving as a correct image, over the entire screen, and learning can be performed using an image on which contrast adjustment appropriate for each region is locally performed. The number of types of image quality improvement processing executable on one screen is not limited to one. Arbitrary image quality improvement processing can be executed by having a plurality of separately-learned models, and one type or a plurality of types of image quality improvement processing can be executed. The image quality improvement processing may be automatically executed in response to a transition to a report screen, or an operator may be allowed to select image quality improvement processing to be executed. In a case where a plurality of types of image quality improvement processing are to be executed, display, to an operator, image quality improvement processing that is executed (color change of button, message display, icon display, checkbox display, etc.).

In the image display on the report screen, an operator can select execution and non-execution of image quality improvement processing described in the present exemplary embodiment, using a user interface (not illustrated) (e.g., button, right click menu, tab switching, checkbox, long tap, multitap, etc.). For example, a case where image quality improvement processing is performed on a tomographic image, a motion contrast tomographic image, and a motion contrast front image (OCTA) will be described with reference to FIG. 14. In FIG. 14, by pressing an image quality improvement button (not illustrated), image quality improvement processing is executed on a tomographic image 1430, the region 1431 related to the motion contrast data, and OCTA images 1401 to 1403, and quality-improved images are displayed. An operator needs not always select execution of image quality improvement processing on a quality-improved image of an OCTA vascular density map, and image quality improvement processing may be automatically executed at a timing at which the operator selects inspection data and a screen transitions to the report screen.

As described in the first to third exemplary embodiments, the image quality improvement processing can also be executed on a time-series screen, which is not illustrated. For example, as described in the third exemplary embodiment, by executing image quality improvement processing on any of time-series fundus images, OCT images, or OCTA images, image quality of time-series images can be collectively improved.

According to the above-described configuration, wide-area OCT images can be captured, and wide-area OCT angiography images can be generated and displayed, and quality-improved images and analysis results can be effectively presented.

In the first to fourth exemplary embodiments, the description has been given of a display configuration in which wide-area OCT images are captured, and analysis results of an optic disk and a macular area, and an analysis result of an OCTA image can be easily recognized. In a fifth exemplary embodiment, the description will be given of an example of displaying data, on one screen, obtained by individually capturing detailed images of an optic disk and a macular area.

As an example, the description will be given with reference to FIG. 5A. In the present exemplary embodiment, data obtained by individually capturing detailed images of an optic disk and a macular area are laid out on one screen as illustrated in FIG. 5A. For example, in FIG. 5A, information regarding images and analysis data 511, 518, 519, 522, 523, 524, and 525 for an optic disk is obtained from data obtained by capturing images of the optic disk, and information regarding other images and analysis data for a macular area is obtained from data obtained by capturing images of the macular area. In a case of displaying data, on one screen, obtained by individually performing image capturing by pressing a data selection button (not illustrated), an operator may select and display optic disk image capturing data or macular area image capturing data. Alternatively, if data obtained by capturing images of an optic disk and a macular area of the same eye on the same day exist on the day selected by the operator, the data selection unit (not illustrated) may automatically select and display data.

According to the above-described configuration, data obtained by individually capturing detailed images of an optic disk and a macular area can be displayed on one screen. Thus, analysis results can be effectively presented without switching data display.

Modification Example 1

In the present exemplary embodiment, processing from image capturing to display has been described as a series of flows, but the processing is not limited to this. For example, analysis may be performed using data already obtained by image capturing. In this case, processing related to image capturing is skipped, and captured images are obtained in place of the processing. With this configuration, report display can be executed as need, without executing analysis processing at the time of image capturing. Thus, it is possible to concentrate only on image capturing at the time of image capturing.

Modification Example 2

In the present exemplary embodiment, the description has been given assuming that data of an optic disk periphery and data of a macular area periphery are separately stored as normative data, but the normative data is not limited to this. For example, if data of wide-area scan including an optic disk and a macular area is stored as normative data, it is sufficient that comparison with the data is performed.

OTHER EMBODIMENTS

Embodiment(s) of the disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Applications No. 2020-170761, filed Oct. 8, 2020, and No.

2020-170762, filed Oct. 8, 2020, which are hereby incorporated by reference herein in their entirety.

What is claimed is:

1. An apparatus comprising:
an obtaining unit configured to obtain, using a coherence tomography, an analysis map related to a disk and an analysis map related to a macular area, which are analysis results of three-dimensional data obtained by capturing an image of a region of a fundus of a subject's eye that includes the disk and the macular area; and
a control unit configured to cause a display unit to display side by side a two-dimensional image related to the region including the disk and the macular area, the analysis map related to the disk, and the analysis map related to the macular area.

2. The apparatus according to claim 1, wherein the control unit displays information indicating a position of the analysis map for the disk, and information indicating a position of the analysis map for the macular area, on the display unit with being superimposed on the two-dimensional image.

3. The apparatus according to claim 1,
wherein the analysis map for the disk is a first comparison map indicating a comparison result of layer thickness information regarding the disk that has been obtained by analyzing the three-dimensional data, and statistical information of a normal eye regarding the disk, and
wherein the analysis map for the macular area is a second comparison map indicating a comparison result of layer thickness information regarding the macular area that has been obtained by analyzing the three-dimensional data, and statistical information of a normal eye regarding the macular area.

4. The apparatus according to claim 3, wherein the two-dimensional image is a front image obtained using at least partial data of the three-dimensional data in a depth direction of the subject's eye, or a layer thickness map obtained by superimposing, on the front image, layer thickness information obtained by analyzing at least partial data of the three-dimensional data in the depth direction of the subject's eye, as color information.

5. The apparatus according to claim 4,
wherein, if either one layer of a layer corresponding to the layer thickness map and a layer corresponding to the second comparison map is switched to a different layer in response to an instruction from an examiner, another layer synchronously switches to the different layer, and display of the layer thickness map and the second comparison map is changed to analysis maps corresponding to the different layer, and
wherein a layer corresponding to the analysis map of the disk is not changed even if the instruction is issued.

6. The apparatus according to claim 1, further comprising an adjustment unit configured to adjust numbers of A scans and B scans in the three-dimensional data by adjusting a position and a size of a partial region in the three-dimensional data to be compared with statistical information of a normal eye, based on a position of the disk or the macular area in the three-dimensional data.

7. The apparatus according to claim 1, wherein, in a plurality of analysis maps for the disk and a plurality of analysis maps for the macular area that are analysis results of a plurality of pieces of three-dimensional data obtained by capturing images of the region including the disk and the macular area at different times using the coherence tomography, the control unit controls the display unit to display the plurality of analysis maps for the disk in time series arranged manner in a first display region, and controls the display unit to display the plurality of analysis maps for the macular area in time series arranged manner in a second display region different from the first display region.

8. The apparatus according to claim 1, wherein the three-dimensional data is a single piece of three-dimensional data obtained by capturing an image of the region including the disk and the macular area.

9. A system comprising:
an ophthalmologic imaging apparatus including a detection unit configured to detect interfering light of return light from a fundus irradiated with measurement light, and reference light, using a coherence tomography; and
the apparatus according to claim 1.

10. A method comprising:
obtaining, using a coherence tomography, an analysis map for a disk and an analysis map for a macular area, which are analysis results of three-dimensional data obtained by capturing an image of a region of a fundus of a subject's eye that includes the disk and the macular area; and
causing a display unit to display side by side a two-dimensional image of the region including the disk and the macular area, the analysis map for the disk, and the analysis map for the macular area.

11. A non-transitory computer-readable storage medium storing a program for causing a computer to execute the method according to claim 10.

* * * * *